United States Patent
Woiceshyn et al.

(10) Patent No.: US 11,507,855 B2
(45) Date of Patent: Nov. 22, 2022

(54) GENERATING ACTION SUGGESTIONS BASED ON A CHANGE IN USER MOOD

(71) Applicant: Motorola Mobility LLC, Chicago, IL (US)

(72) Inventors: Leo S. Woiceshyn, Chicago, IL (US); Yi Wu, Chicago, IL (US); Thomas Yates Merrell, St Charles, IL (US); Zhengping Ji, Hinsdale, IL (US)

(73) Assignee: Motorola Mobility LLC, Chicago, IL (US)

( * ) Notice: Subject to any disclaimer, the term of this patent is extended or adjusted under 35 U.S.C. 154(b) by 880 days.

(21) Appl. No.: 16/362,454

(22) Filed: Mar. 22, 2019

(65) Prior Publication Data
US 2020/0302310 A1 Sep. 24, 2020

(51) Int. Cl.
*G16H 20/70* (2018.01)
*G06N 5/04* (2006.01)
*G06K 7/14* (2006.01)
*G06N 20/00* (2019.01)
*G16H 50/20* (2018.01)

(52) U.S. Cl.
CPC ............. *G06N 5/04* (2013.01); *G06K 7/1413* (2013.01); *G06N 20/00* (2019.01); *G16H 50/20* (2018.01)

(58) Field of Classification Search
CPC .................................................. G06F 16/9535
See application file for complete search history.

(56) References Cited

U.S. PATENT DOCUMENTS

| | | | | |
|---|---|---|---|---|
| 2016/0170946 A1* | 6/2016 | Lee | ...................... | G06F 3/04842 715/234 |
| 2016/0350514 A1* | 12/2016 | Rajendran | ............... | G16H 20/60 |
| 2017/0333666 A1* | 11/2017 | Goldberg | ................ | A61B 5/165 |
| 2018/0357473 A1* | 12/2018 | Soma | ..................... | B60W 40/00 |
| 2019/0276037 A1* | 9/2019 | Ito | ...................... | B60W 50/0097 |
| 2020/0068434 A1* | 2/2020 | Pedersen | ................. | H04L 67/12 |

(Continued)

OTHER PUBLICATIONS

"Daylio—Journal, Diary, Moods—App", Retrieved at: https://itunes.apple.com/us/app/daylio-journal-diary-moods/id1194023242?mt=8—on Nov. 21, 2018, 2 pages.

(Continued)

*Primary Examiner* — Di Xiao
(74) *Attorney, Agent, or Firm* — FIG. 1 Patents

(57) ABSTRACT

In aspects of generating action suggestions based on a change in user mood, a computing device implements an action generation module that generates action suggestions. The action generation module analyzes sensor data from sensors to determine a current user state associated with a user. The action generation module also analyzes environment data received from Internet-of-Things (IoT) devices to determine a current environment context associated with the user. The action generation module can detect a change in a user mood based on a comparison of the current user state with user history data that includes user state parameters and environment context parameters that indicate the user mood. The action generation module can analyze the user history data to determine the user state parameters and/or the environment context parameters that correlate to the change in the user mood, and generate an action suggestion that is intended to modify the current user state.

20 Claims, 11 Drawing Sheets

(56) References Cited

U.S. PATENT DOCUMENTS

2020/0139077 A1* 5/2020 Biradar .................. G10L 25/63
2020/0160386 A1* 5/2020 Chan .................. G06Q 30/0269

OTHER PUBLICATIONS

"Emotion Detection from Speech Signals—YouTube", Retrieved at: https://www.youtube.com/watch?v=RbfGmX8Qrbg, Jul. 27, 2016, 1 page.

"Exist App", Retrieved at: https://exist.io/—on Nov. 21, 2018, 11 pages.

"How the Light in a Room Could Affect Your Emotions", https://www.huffpost.com/entry/light-emotions_n_4831224, Feb. 24, 2014, 3 pages.

Chernykh,"Emotion Recognition from Speech with Recurrent Neural Networks", Jul. 5, 2018, 18 pages.

Choi,"Mood-Detecting Sensor Could Help Machines Respond to Emotions—Smart homes could play music to fit your mood", https://spectrum.ieee.org/the-human-os/robotics/robotics-hardware/mooddetecting-sensor-could-help-machines-respond-to-emotions, Sep. 20, 2016, 2 pages.

Doerrfeld,"20+ Emotion Recognition APIs That Will Leave You Impressed, and Concerned", https://nordicapis.com/20-emotion-recognition-apis-that-will-leave-you-impressed-and-concerned/, Dec. 31, 2015, 22 pages.

Kleinberger,"Why you don't like the sound of your own voice", Retrieved at: https://www.youtube.com/watch?v=g3vSYbT1Aco, May 24, 2018, 1 page.

Knapton,"Bad mood? New app senses emotion and suggests food to lift spirits", https://www.telegraph.co.uk/science/2016/11/27/bad-mood-new-app-senses-emotion-suggests-food-lift-spirits/, Nov. 27, 2016, 3 pages.

Picard,"Toward Computers that Recognize and Respond to User Emotion", Dec. 2000, pp. 705-719.

Prodhan,"Passive Mood Tracking with the Feel Wristband", Retrieved at: https://emberify.com/blog/mood-tracking-wearable-feel-wristband/, Jun. 2, 2016, 7 pages.

Zagaki,"INSCAPE: Emotion Expression and Experience in an Authoring Environment", Dec. 2006, 12 pages.

\* cited by examiner

Weighting Table for Action Suggestions — 800

| | |
|---|---|
| Biometric Data | 0.75 |
| Environment Data | 0.5 |
| Location Data | 0.4 |
| Peer Data | 0.25 |
| Mood Data | 0.65 |

Weighting Table for Action Suggestions — 802

| Location | Number of Visits | Priority |
|---|---|---|
| Location A | 1 | 0.05 |
| Location B | 50 | .2 |
| Location C | 375 | 1 |
| Location D | 4 | 0.1 |
| Location E | 183 | 0.75 |

FIG. 8

GENERATING ACTION SUGGESTIONS BASED ON A CHANGE IN USER MOOD

BACKGROUND

A user's mood can be influenced by many different environmental factors. For example, on a cold day, the user moving into a warm-temperature room can improve the user's mood, while on a hot day, moving into the warm-temperature room can diminish the user's mood. Thus, the user's mood can be influenced not only based on a current environment context (e.g. the warm-temperature room), but an additional environment context corresponding to the day's ambient-temperature. In view of the additional environment context, the user is likely to be content in the warm-temperature room on the cold day and irritable on the hot day. Other external factors that are not immediately linked to the user can also influence a current mood, such as a lack of sleep the prior night, what the user ate for breakfast three hours prior to the current mood, and so forth. These external factors can be nonobvious to the user, so much so, the user is unable to discern past events, like the poor breakfast, contributing to a current (negative) mood later in the day. Without the additional context information, a current environment context (e.g., the warm-temperature room) does not provide enough information to identify a source of the user's diminished mood.

BRIEF DESCRIPTION OF THE DRAWINGS

Implementations of generating action suggestions based on a change in user mood are described with reference to the following Figures. The same numbers may be used throughout to reference similar features and components that are shown in the Figures:

FIG. 8 illustrates example weighting tables that can be utilized in aspects of generating action suggestions based on a change in user mood.

DETAILED DESCRIPTION

Figure 1:
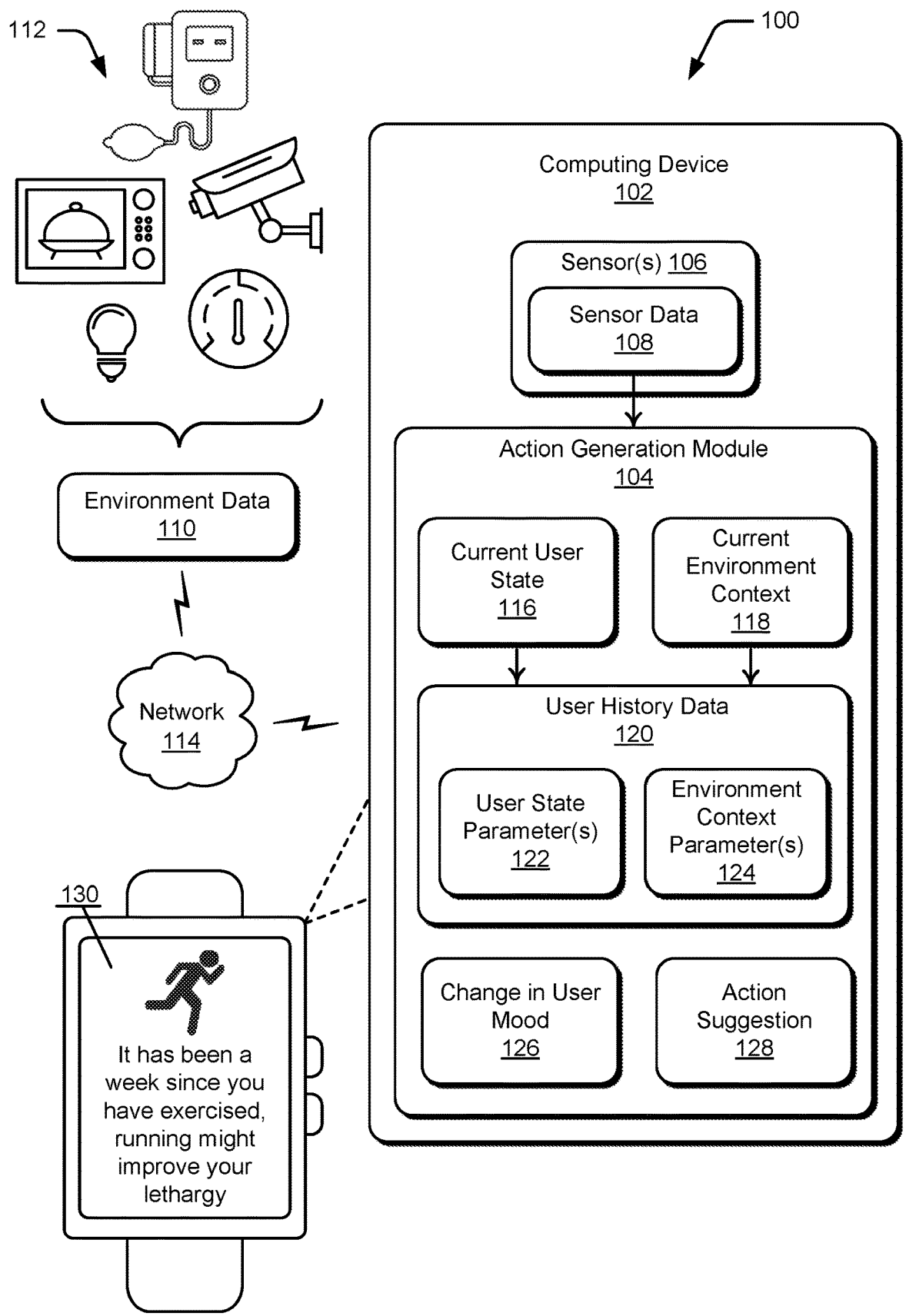
FIG. 1 illustrates an example environment in which aspects of generating action suggestions based on a change in user mood can be implemented.

Aspects of generating action suggestions based on a change in user mood are described, and provide a system for the dynamic generation of an action suggestion based on detecting a change in user mood. Generally, generating a mood-based action suggestion refers to identifying and/or predicting an action particular to a user that is intended to modify a mood state of the user, such as through an analysis of past user state parameters and/or past environment context parameters.

An action generation module compiles user history data over a duration, such as hours, a day, a week, a number of years, etc., where the user history data includes the past user state parameters and the past environment context parameters. Generally, user state parameters correspond to information about a particular user, such as a mood state parameter, an activity state parameter identified as being active or inactive, and so forth. Environment context parameters correspond to information that provides additional context about the particular user, such as parameters that indicate a location context, an activity type context, an environment temperature context, and so on. The action generation module can determine a current user state and/or a current environment context of a user based on sensor data, such as sensor data received from sensors of a mobile device, and based on environment data received from Internet of Things (IoT) devices, where the current user state and/or the current environment context can indicate a user mood associated with the user.

The action generation module can aggregate the current user state and the current environment context with the user state parameters and the environment context parameters to compile updated user history data. Thus, the updated user history data can include instantaneous (current) data compiled from the sensor data and the environment data, and a collection of past user state parameters and past environment context parameters compiled over an arbitrary duration (e.g., an hour, a day, a week, a month, a year, multiple years, etc.). The aggregation of user history data allows the action generation module to improve the action suggestions that are generated because the action generation module can analyze the large volumes of data to identify past user moods and past environment parameters that may correlate to a current change in user mood. In turn, the action generation module can generate action suggestions with a higher probability of modifying the mood state of the user relative to other action suggestions based on the past user moods and the past environment parameters.

In implementations, the action generation module can identify correlations between a user state and environment context parameters, such as through the use of various machine-learning algorithms. For example, the action generation module can apply machine-learning algorithms to the user history data to identify a sequence of user mood state changes, and then correlate the sequence of the user mood state changes to a sequence of the environment context parameters. The action generation module can then update user history data to link the sequence of the user mood state changes with the sequence of the environment context parameters. By updating the user history data with linkages between the sequence of the user mood state changes and the sequence of the environment context parameters, the action generation module stores user-specific information that describes how different environment changes affect the user's mood. Further, the inclusion of environment data from IoT devices augments the user-specific information by providing additional context that would not be considered otherwise. The action generation module can use this user-specific information at a later point in time to determine an action suggestion directed towards the user. This differs from action suggestions generated on instantaneous data insofar as the instantaneous data lacks a history of user-specific information that can provide additional context into the user as described herein.

The action generation module can also apply machine-learning algorithms to identify a correlation between the current user state and a current environment context, and update the user history data by adding the correlation between the current user state and the current context environment to the user history data. The usage of machine-learning algorithms can improve the overall operation of a computing device that implements the action generation module by learning and improving what correlations are identified between the user state parameters and the environment context parameters, by using (and updating) the learned information to improve the data analyses times (e.g., faster analysis), and by generating more accurate mood-based action suggestions, thus improving a quality of an output generated by the computing device.

In implementations, the action generation module receives sensor data from sensors of a computing device implementing the action generation module, and determines a current user state based on the sensor data. Alternately or in addition, the action generation module receives environment data from IoT devices, such as appliances, televisions, speakers, toys, meters, security systems, weather monitors, exercise equipment, health monitors, lights, home devices, door locks, trackers, thermostats, and so forth. Each respective IoT device and/or smart device can include varying types of sensors to collect environment data that provides metrics about a surrounding environment (e.g., light level, noise level, activity identifier, location identifier, temperatures, etc.). The action generation module receives the environment data from the IoT devices, and analyzes the environment data to determine a current environment context. This differs from action suggestions based on sensor data alone insofar as the addition of the environment data from the IoT devices increases the amount of information analyzed by the action generation module, provides more context information about the user, and improves the accuracy of the generated action suggestion as described herein.

In other aspects of generating action suggestions based on a change in user mood, the action generation module can prioritize the current user state, the current environment context, and/or the user history data as a way to improve the accuracy of the generated action suggestion. As one example, the action generation module can apply the weighting data to the environment data, the sensor data, the current user state, the current environment, and/or the user history data, where the weighting data prioritizes data based on location (e.g. data acquired from more frequently visited locations is prioritized higher than data acquired from less frequently visited locations). The action generation module can then analyze the prioritized data to determine user state parameters and/or environment context parameters that correlate to a change in user mood. This can improve the action suggestion generated by the action generation module by reducing an importance of data corresponding to anomalies, thus reducing the variation in data analysis introduced by the anomalies.

While features and concepts of generating action suggestions based on a change in user mood can be implemented in any number of different devices, systems, networks, environments, and/or configurations, implementations of action generation modules are described in the context of the following example devices, systems, and methods.

FIG. 1 illustrates an example environment 100 in which aspects of generating action suggestions based on a change in user mood can be implemented. The example environment 100 includes a computing device 102, which implements features of an action generation module 104 as described herein. The computing device 102 can be implemented as any type of computing device, client device, mobile phone, tablet device, communication device, entertainment device, gaming device, media playback device, and/or other type of electronic and/or computing device. In implementations, the computing device 102 can be implemented as a wearable computing device, such as a watch, armband, wristband, bracelet, glove or pair of gloves, glasses, jewelry items, clothing items, any type of footwear or headwear, and/or other types of wearables. In the example environment 100, the computing device 102 may include any number and combination of different components as shown and described with reference to the example device shown in FIG. 11.

The computing device 102 implements the action generation module 104, such as in software, in hardware, or as a combination of software and hardware components. In this example, the action generation module 104 is implemented as a software application or module, such as executable software instructions (e.g., computer-executable instructions) that are executable with a processing system of the computing device 102 to implement the techniques of generating an action suggestion based on a change in user mood. The action generation module 104 can be stored on computer-readable storage media, such as any suitable memory device or electronic data storage implemented in the computing device 102. Alternately or in addition, the action generation module 104 may include independent processing, memory, and logic components functioning as a computing and/or electronic device integrated with the computing device The action generation module 104 receives various types of data as input and generates user mood and contextual information from the data. In the example environment 100, the computing device 102 includes sensors 106 that generate sensor data 108. The sensors 106 represent any type of sensor that can be used to measure and/or collect information, such as cameras, microphones, biometric sensors (e.g., heartrate sensors, body temperature sensors, fingerprint sensors, iris sensors, sleep sensors, electrodermal activity sensors, etc.), accelerometers, gyroscopes, and so forth. Each sensor of the sensors 106 can produce a portion or all of the sensor data 108 that is input to, and analyzed by, the action generation module 104. For example, a camera can capture an image that is input to the action generation module and analyzed for facial expressions. A microphone can capture audio that is input to the action generation module and analyzed for voice intonations. As yet another example, a biometric sensor can capture heartrate information that is analyzed for mood symptoms. Thus, the sensor data 108 represents a variety of data that can be obtained from various sensors. Alternately or in addition, the computing device 102 can receive environment data 110 produced by IoT devices 112 by way of network 114.

The IoT devices 112 generally represent computing devices with connectivity to a network. In implementations, an IoT device can be a computing device dedicated to particular functionality, such as a light bulb that can be accessible over the network to control the luminance of the light bulb and/or to obtain operation reports (e.g., on, off, duration, luminance level, etc.). The IoT devices 112 can include any combination of devices, such as a home appliance, a biometric sensor, a security camera, a thermostat, a controller, a light bulb, exercise equipment, a motorized vehicle, a speaker, a game controller, and so forth. In turn, the environment data 110 produced by each respective IoT device can vary. For example, an IoT microwave can provide environment data that includes barcode information of food being cooked in the microwave, while an IoT thermostat can provide environment data that includes temperature information. In implementations, the computing device 102 maintains a list of the IoT devices 112 to access in order to obtain the environment data 110. Alternately or in addition, an IoT device 112 can advertise its presence over the network 114 such that the computing device 102 can automatically identify and connect to the IoT device when moving within working range of the IoT device (e.g., can successfully exchange data with the IoT device). Thus, the combination of devices included in the IoT devices 112 can vary over time and/or location.

The network 114 represents any type of network that can be used to facilitate communications between computing devices, such as the IoT devices 112 and the computing device 102. The network can be implemented to include a wired and/or a wireless network. The network can also be implemented using any type of network topology and/or communication protocol, and can be represented or otherwise implemented as a combination of two or more networks, to include IP-based networks and/or the Internet. The network may also include mobile operator networks that are managed by a mobile network operator and/or other network operators, such as a communication service provider, mobile phone provider, and/or Internet service provider. In implementations, the network 114 can include an IoT network, such as Zibgee, Z-wave, Thread, Weave, etc.

The action generation module 104 can analyze the sensor data 108 and the environment data 110 to determine a current user state 116 and a current environment context 118. In implementations, the current user state 116 includes user mood state information that indicates a current mood of a user (e.g., bored, excited, sleepy, content, discontent, annoyed, angry, depressed, tired, happy, lethargic, bored, etc.). The current environment context 118 can include any combination of data that provides a current context, such as a current location, a current temperature, a current activity, a transition in location, a current sound level, a current light level, etc. To determine the current user state and the current environment context, the action generation module 104 can include any combination of machine-learning algorithms, such as Natural Language Processing (NLP) algorithms, Deep Learning Algorithms (Neural Networks, Convolutional Neural Networks, Recurrent Neural Networks), Active Appearance Models, Support-vector networks, cluster analysis algorithms, association rule learning, anomaly detection algorithms, regression analysis algorithms, classification algorithms, summarization algorithms, ensemble algorithms, regularization algorithms, rule system algorithms, regression algorithms, Bayesian algorithms, decision tree algorithms, dimensionality reduction algorithms, Instance based algorithms, K-nearest neighbors algorithms, gradient descent algorithms, linear discriminant analysis, classification and regression trees, learning vector quantization, Bagged Decision Trees, Random Forest algorithms, boosting, etc. In implementations, the machine-learning algorithms can be trained using existing datasets, such as the Extended Cohn-Kanade Dataset, the Physikalisch-Technische Bundesanstalt (PTB) database, etc., to recognize emotions.

The action generation module 104 can also include user history data 120 that represents data about a user that has been collected over a duration. The duration can be any arbitrary length in time, such as an hour, a day, multiple days, multiple weeks, multiple months, multiple years, and so forth. In implementations, the action generation module 104 updates the user history data 120 by combining and/or adding the current user state 116 and the current environment context 118 to the user history data 120. Thus, the action generation module 104 can continuously update the user history data 120 by updating the data each time the current user state 116 and/or the current environment context 118 is determined. The user history data 120 includes user state parameters 122 and environment context parameters 124, where the user state parameters 122 represent a history and/or collection of user state data over the duration, and the environment context parameters 124 represent a history and/or collection of environment context data over the duration. The user history data 120 can alternately or in addition include correlation information that identifies linkages between particular user state parameters and particular environment context parameters as further described herein.

In implementations, the action generation module 104 can detect a change in user mood 126. For example, the action generation module 104 can compare the current user state 116 with the user history data 120 (e.g., the user state parameters 122) and determine that a user mood indicated by the current user state 116 has changed from a prior user mood indicated by the user history data 120. The action generation module 104 can then analyze the current user state 116, the current environment context 118, and/or the user history data 120 to identify at least one user state parameter or environment context parameter that corresponds to the change in user mood 126. For example, the action generation module 104 can apply machine-learning algorithm(s) to identify particular user state parameter(s) and/or environment context parameter(s) with a higher probability and/or correlation to causing the change in mood relative to other user state parameters and/or environment context parameters(s) Thus, the action generation module 104 can analyze instantaneous, short-term results based on the sensor data and/or the environment data (e.g., the current user state, the current environment context) and longer-term results acquired over an arbitrary duration (e.g. user history data). The inclusion of the user history data 120 provides more user state and environment context information that helps improve the accuracy of identifying a potential cause to the change in user mood as described herein.

In response to identifying the particular user state parameter(s) and/or particular environment context parameter(s) with the higher probability and/or correlation to causing the change in mood, the action generation module 104 generates an action suggestion 128 that is intended to modify the current user state 116. In implementations, the action generation module 104 can include machine-learning algorithms and/or recommender systems to identify an action to suggest. For example, the action generation module can include a content-based recommender system that bases an action suggestion on the particular user state parameter(s), the particular environment context parameter(s), the user history data, and/or past actions that have successfully modified a user's mood as indicated by a user state. Alternately or in addition, the action generation module can include a collaborative filtering-based recommender system that bases an action suggestion on other user profiles and/or other user data that has been identified as being similar to the user. In implementations, the action generation module 104 can output the action suggestion 128 as an audible message, a visual message, and so forth. In the example environment 100, the action generation module outputs the action suggestion 128 as a visual display 130.

Figure 2:
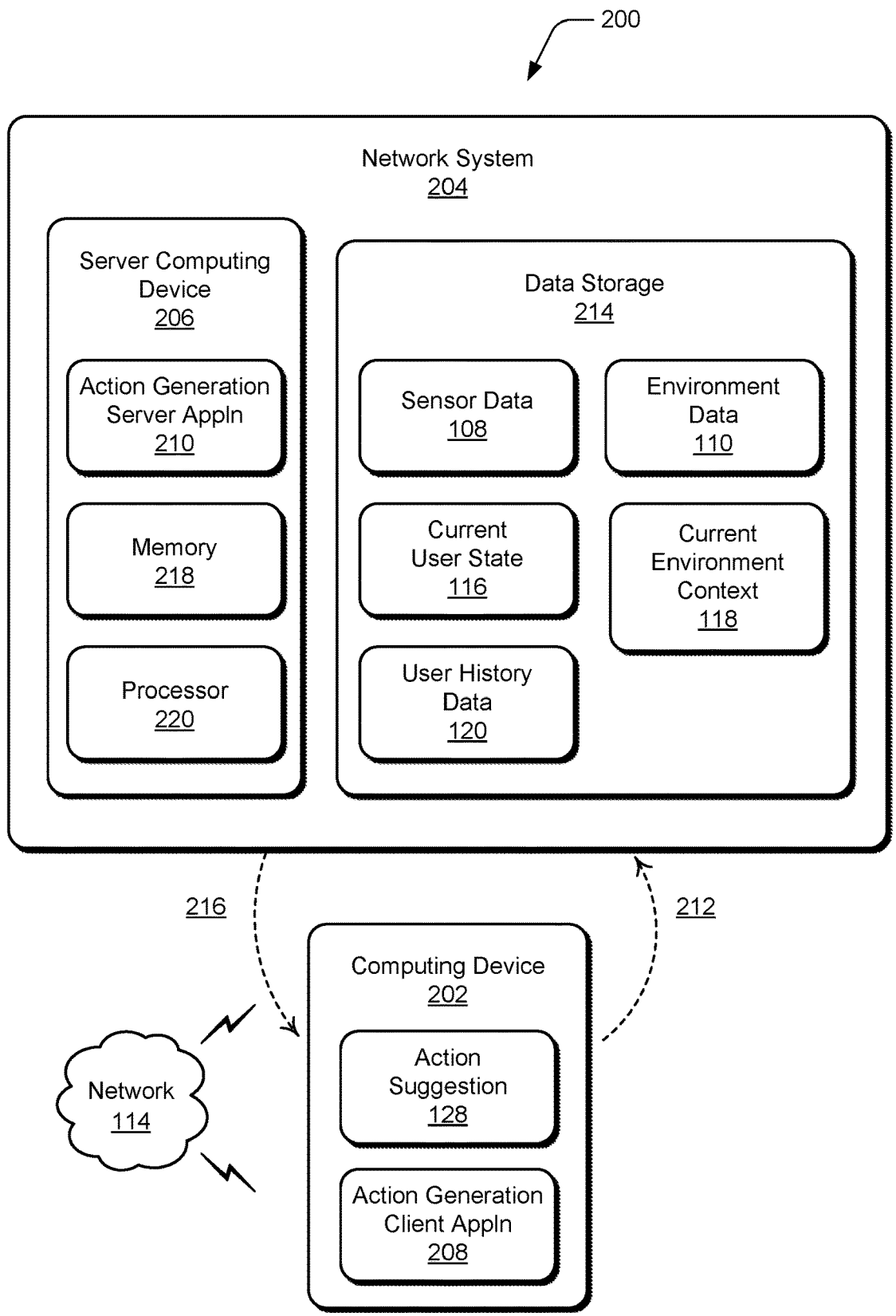
FIG. 2 illustrates an example environment in which aspects of generating action suggestions based on a change in user mood can be implemented.

FIG. 2 illustrates another example environment 200 in which aspects of generating action suggestions based on a change in user mood can be implemented. The example environment 200 includes a computing device 202 and a network system 204, which implements features of the action generation module 104 of FIG. 1. The computing device 202 can be implemented as any type of computing device described herein, such as the computing device 102 shown and described with reference to FIG. 1. In this example environment 200, the computing device 202 may include any number and combination of different components as shown and described with reference to the example device shown in FIG. 11, and is implemented to access and communicate with a server computing device 206 of the network system 204, such as via the network 114. Examples of the network 114 are described with reference to FIG. 1 and any of the devices, servers, and/or services described herein can communicate via the network 114, such as data communication between the computing device 202 and the network system 204.

In this example environment 200, the computing device 202 includes an action generation client application 208 that corresponds to a client-side implementation of the action generation module 104 shown and described with reference to FIG. 1. The action generation client application 208 can communicate with an action generation server application 210 at the server computing device 206 over the network 114, where the action generation server application 210 corresponds to a server-side implementation of the action generation module 104.

A user of the computing device 202 may upload the sensor data 108 to the network system 204, as indicated at 212, and the sensor data 10 may be stored in data storage 214 of the network system. The network system 204 can receive the uploaded sensor data 108 as input to the action generation server application 210. Similarly, the computing device 202 may upload the environment data 110 to the network system 204, such as the environment data received by the computing device from the IoT devices 112. Alternatively or in addition, the network system 204 may receive the environment data 110 directly from various IoT devices that are generally associated with or correspond to the computing device 202. The action generation server application 210 can analyze the sensor data 108 and/or the environment data 110 to determine the current user state 116, the current environment context 118, and/or the action suggestion 128. In implementations, the action generation server application 210 can also update the user history data 120 to include the current environment context 118 and/or the current user state 116 as described herein.

Notably, the server computing device 206 can communicate the action suggestion 128 from the network system 204 to the computing device 202 via the network 114, as indicated at 216, where the action suggestion 128 can be displayed for the user, such as in a device user interface. In receiving the action suggestion 128, the action generation client application 208 can display and/or audibly output the action suggestion to the user. In implementations, the exchanges between the network system 204 and the computing device 202 can occur automatically and without a user initiating the process, although the user can alternatively request an action suggestion. Thus, the action generation server application 210 implemented at the network system 204 can detect a change in user mood, and generate action suggestions that are communicated to the user of the computing device 202, where the action suggestions are intended to address the change in user mood, such as action suggestions directed towards modifying a discontented mood to a contented mood.

In this example environment 200, the network system 204 is representative of any number of cloud-based access sites that provide a service and/or from which data and information is available, such as via the Internet, for on-line and/or network-based access. The cloud-based services can be implemented using any suitable type of cloud-based service and/or deployment mechanism across a network, such as cloud-based services that follow, by way of example and not limitation, a Software as a Service (SaaS) model, a Platform as a Service (PaaS) model, an Infrastructure as a Service (IaaS) model, and so forth. Accordingly, the various implementations described herein can be deployed and/or implemented using any one or combination of these models to generate action suggestions based on a change in user mood. The network system 204 can be accessed on-line, and includes the server computing device 206, which is representative of one or more hardware server devices (e.g., computing devices) that may be implemented at the network system. The server computing device 206 includes memory 218 and a processor 220, and may include any number and combination of different components as shown and described with reference to the example device shown in FIG. 11.

In this example environment 200, the server computing device 206 implements the action generation server application 210, such as in software, in hardware, or as a combination of software and hardware components, as shown and described with reference to the example device shown in FIG. 11. In this example, the action generation server application 210 is implemented as a software application or modules, such as executable software instructions (e.g., computer-executable instructions) that are executable with a processing system (e.g., the processor 220) of the server computing device 206 to implement the techniques of generating action suggestions based on a change in user mood. The action generation server application 210 can be stored on computer-readable storage media, such as any suitable memory device (e.g., the device memory 218) or electronic data storage implemented in the server computing device 206 and/or at the network system 204.

The network system 204 may include multiple data storage, server devices, and applications, and can be implemented with various components as shown and described with reference to the example device shown in FIG. 11. The network system 204 also includes the data storage 214 that may be implemented as any suitable memory, memory device, or electronic data storage for network-based data storage. The data storage 214 is utilized at the network system 204 to maintain any combination of the sensor data 108, the environment data 110, the current user state 116, the current environment context 118, and/or the user history data 120 as shown and described with reference to FIG. 1.

Using network-based implementations to generate action suggestions based on a change in user mood helps conserve the resources of a corresponding user device, such as computing device 202. The action generation client application 208, for example, can offload machine-learning computations to the action generation server application 210, thus freeing up processor cycles at the computing device 202 for other applications. Alternately or additionally, the action generation client application 208 can offload any combination of the sensor data, the environment data, and/or the user history data to the network system 204, thus freeing up data storage at the computing device 202 for other applications.

Figure 3:
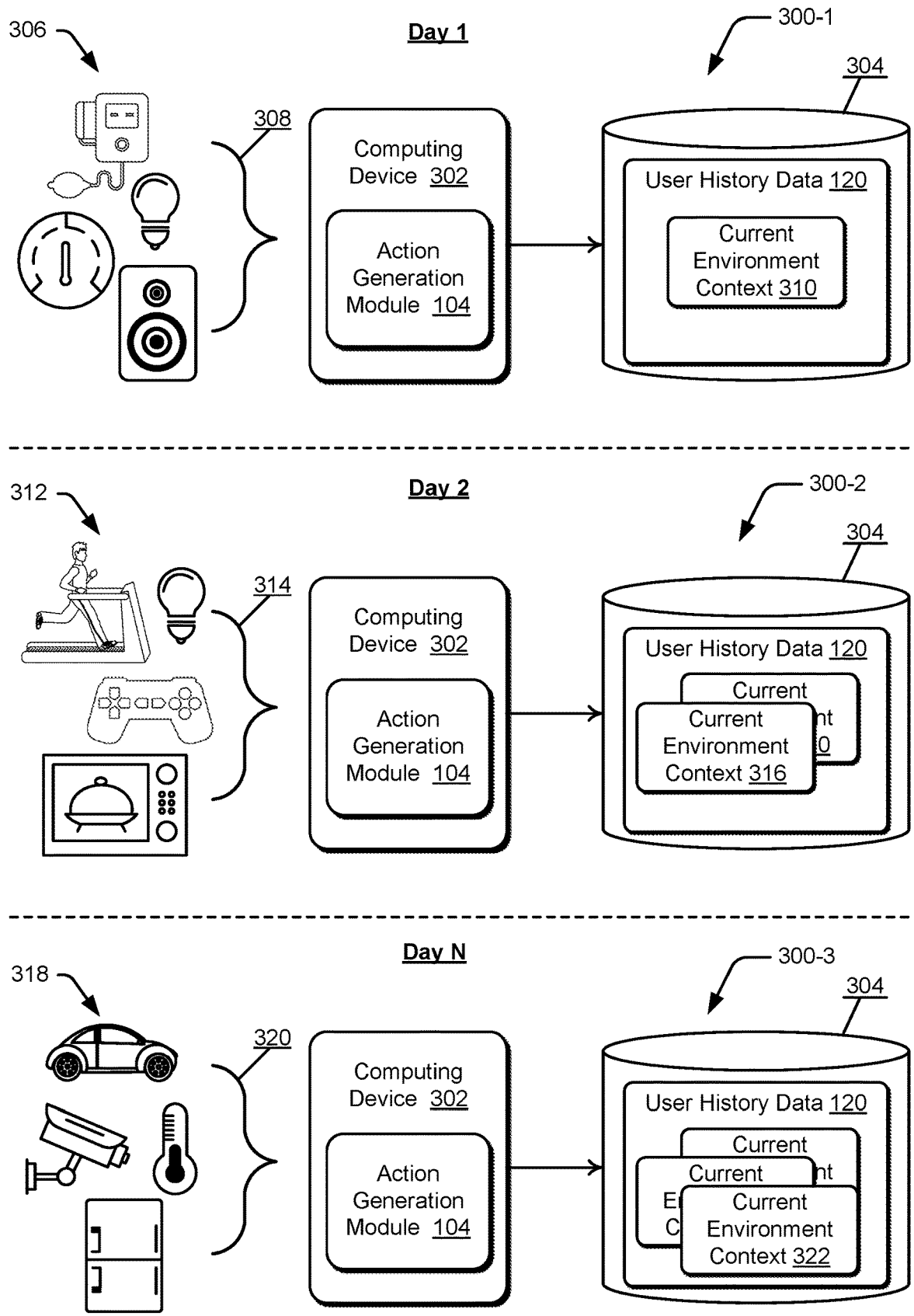
FIG. 3 illustrates an example environment in which aspects of generating action suggestions based on a change in user mood can be implemented.

FIG. 3 illustrates an example environment 300 in which a progression of events implements aspects of generating action suggestions based on a change in user mood. These events occur in an example environment 300 that includes a computing device 302. The example environment 300 is represented at three arbitrary points in time that are labeled as example environment 300-1, example environment 300-2, and example environment 300-3, respectively. The example environment 300-1 corresponds to a first point in time labeled as "Day 1", the example environment 300-2 corresponds to a second point in time labeled as "Day 2", and the example environment 300-3 corresponds to an arbitrary point in time labeled as "Day N", where "N" is an arbitrary number. Collectively, the example environments 300-1, 300-2, and 300-3 embody the example environment 300.

The computing device 302 can be any suitable type of computing device that implements the action generation module 104 as shown and described with reference to FIG. 1 to generate action suggestions based on a change in user mood. In implementations, the computing device 302 is representative of the computing device 102 (FIG. 1), the computing device 202 (FIG. 2), or the server computing device 206 (FIG. 2). The environment 300 also includes the user history data 120 of FIG. 1 that is maintained on a storage device 304, where example storage devices are described with reference to the example device 1100 of FIG. 11. While the user history data 120 is illustrated external to the computing device 302 in the example environment 300, implementations of the computing device 302 store the user history data 120 internal to the computing device, such as on memory devices as described herein.

The example environment 300-1 represents a point in time (e.g., "Day 1") where the computing device 302 is positioned at a location that includes devices 306. The devices 306 can be any suitable type of device that has the ability to collect and exchange data with another computing device, such as any combination of IoT devices external to the computing device 302 and/or sensors internal to the computing device 302. In the example environment 300-1, the computing device 302 has established a communication link to some or all of the devices 306, such as over a wireless communication link, a wired communication link, an internal communication bus, via shared memory, etc. The devices 306 include a speaker, a light bulb, a thermostat, and a biometric sensor, each of which has an ability to collect and communicate environment data to other devices. The devices 306 can collect and transmit the environment data as input 308 to the computing device 302 and/or the action generation module 104. The environment data can be collected and/or transmitted by the devices on a periodic basis, on a continuous basis, based on user input, based on environmental triggers (e.g. a change in room temperature, ambient noise levels, luminosity, etc.), asynchronously from one another, and so forth. In implementations, the computing device 302 can poll or query the devices 306 to obtain the input 308. The combination of devices included in the devices 306 can be a fixed combination of devices and/or can be a dynamically changing combination of devices that are in communication with the computing device 302.

In implementations, the computing device 302 automatically establishes a communication link with the devices 306 without receiving explicit user input directed towards establishing the communication link. For example, the computing device 302 can identify IoT devices by an auto-registration process, such as by connecting to a hub and establishing a connection to any IoT devices connected to the hub. Alternately or in addition, the computing device can maintain a list of IoT devices at respective locations and attempt to connect to the IoT devices based on a current location. In implementations, an IoT device can wirelessly advertise its presence. As the computing device 302 moves within range of the IoT device, the computing device can receive the advertisement and initiate a connection to the IoT device. The computing device 302 can also maintain a record of connections to IoT devices and generate metrics utilized to identify which devices are more frequently in communication with the computing device, which connections (and corresponding environment data) are new to the computing device, etc. These metrics can then be utilized to weight the environment data received from the IoT devices, such as by weighting environment data received from devices and/or locations less frequented by the computing device 302 lower, and weighting environment data received from devices and/or locations more frequented by the computing device 302 higher. Alternately or in addition, a user can manually connect the computing device 302 to an IoT device.

The action generation module 104 analyzes the input 308 and determines a current environment context 310 as described herein. For example, the action generation module 104 can apply machine-learning algorithm(s) to the input 308 to identify that the current room temperature has increased, that the current audio level is at 75 decibels (dBs), that a speaker is playing a song that a user enjoys, that the lights in the room are on, and so forth. Thus, the current environment context 310 is representative of instantaneous and/or a current environment context determined from the input 308, and can include context data that identifies a change in the environment. In response to determining the current environment context 310, the action generation module 104 adds and/or aggregates the corresponding data to the user history data 120, such as by storing the current environment context 310 as environment context parameters within the user history data. This can include storing timestamps, date information, location information, and so forth, with the current environment context in the user history data.

The example environment 300-2 corresponds to a second point in time (e.g., "Day 2") where the computing device 302 is positioned at a location that includes devices 312. The location of the example environment 300-2 can be the same location as that described with respect to the example environment 300-1, or a different location. The devices 312 can include any combination of devices, such as IoT devices external to the computing device 302 and/or sensors internal to the computing device 302. The devices 312 can include some or all of the devices 306 in the example environment 300-1. In the example environment 300-2, the devices 312 include exercise equipment, a light bulb, a kitchen appliance, and a gaming controller, each of which has an ability to collect and communicate environment data to the computing device. For example, the exercise equipment can collect environment data that includes an exercise identifier that indicates a corresponding exercise activity, when the exercise activity is occurring, when the exercise activity is not occurring, a pace of the exercise activity, a duration of the exercise activity, calories burned during the exercise activity, etc. In some implementations, the exercise equipment can include biometric sensors, such as a heartrate monitor, and collect heartbeat information as environment data. As another example, a smart microwave can scan barcode information to automatically determine cooking settings for a particular food item. In turn, the smart microwave can forward the barcode information associated with the food item as environment data.

Similar to that described with respect to the example environment 300-1, the devices 312 represent a group of devices that can dynamically change over time. In the example environment 300-2, the action generation module 104 receives input 314 from the devices 312. The input 314 generally represents environment data that can be transmitted to the computing device 302 at any rate, frequency, and/or quantity as described herein, such as environment data produced by respective devices of the devices 312 that is transmitted at asynchronous points in time. The action generation module 104 determines current environment context 316 based on the input 314. For example, in response to receiving barcode information of a food item as the input, the action generation module can use the barcode information to access a server that stores nutritional information associated with the food item and determine a health metric associated with the food item (e.g., healthy, unhealthy) as the current environment context. The action generation module 104 then aggregates the user history data 120 with the environment context determined in the example environment 300-2, such as by storing the current environment context 316 as environment context parameters within the user history data. This can include storing timestamps, date information, location information, and so forth, with the current environment context in the user history data. Thus, in the example environment 300-2, the user history data 120 has been updated to include the current environment context 310 determined in the example environment 300-1 and the current environment context 316.

The example environment 300-3 corresponds to an arbitrary point in time (e.g., "Day N") where the computing device 302 is positioned at a location that includes devices 318. In the example environment 300-3, the devices 318 include a smart car, a smart camera, a biometric temperature sensor, and a smart appliance, each of which has an ability to collect and communicate environment data to the computing device. For example, the camera can collect environment data that includes images and/or video that is forwarded to the computing device 302, a notification of when motion is detected, a notification of facial recognition, etc. As another example, the smart car can forward location information, an indication of the smart car being stationary, and indication of the smart car being mobile, etc., as environment data. As yet another example, the biometric temperature sensor can forward a body temperature as environment data.

Similar to that described with respect to the example environment 300-1 and/or the example environment 300-2, the devices 318 can include any combination of devices, including some, all, or none of the devices 312 and/or the devices 306. The location associated with the example environment 300-3 can be the same location corresponding to the example environment 300-1, the same location corresponding to the example environment 300-2, or a different location. In response to receiving input 320 from the devices 318, the action generation module 104 determines current environment context 322, such as by analyzing location information received from the smart car to determine an environment context that indicates the location corresponds to a work location, a home location, a restaurant, etc. As another example, the action generation module 104 can analyze a still image produced by a smart camera to identify a person in the image, and determine an environment context that indicates a particular person is present.

The action generation module 104 aggregates the current environment context 322 with the user history data 120, such as by storing the current environment context 322 as environment context parameters within the user history data. This can include storing timestamps, date information, location information, and so forth, with the current environment context 322 in the user history data. In the example environment 300-3, the user history data 120 has been updated to include the current environment context 310 determined in the example environment 300-1, the current environment context 316 determined in the example environment 300-2, and the current environment context 322. Thus, the action generation module can receive environment data from a variety of devices and/or sensors, determine a current environment context based on the environment data, and aggregate the user history data to include a collection of environment context data that has been gathered over an arbitrary duration.

Figure 4:
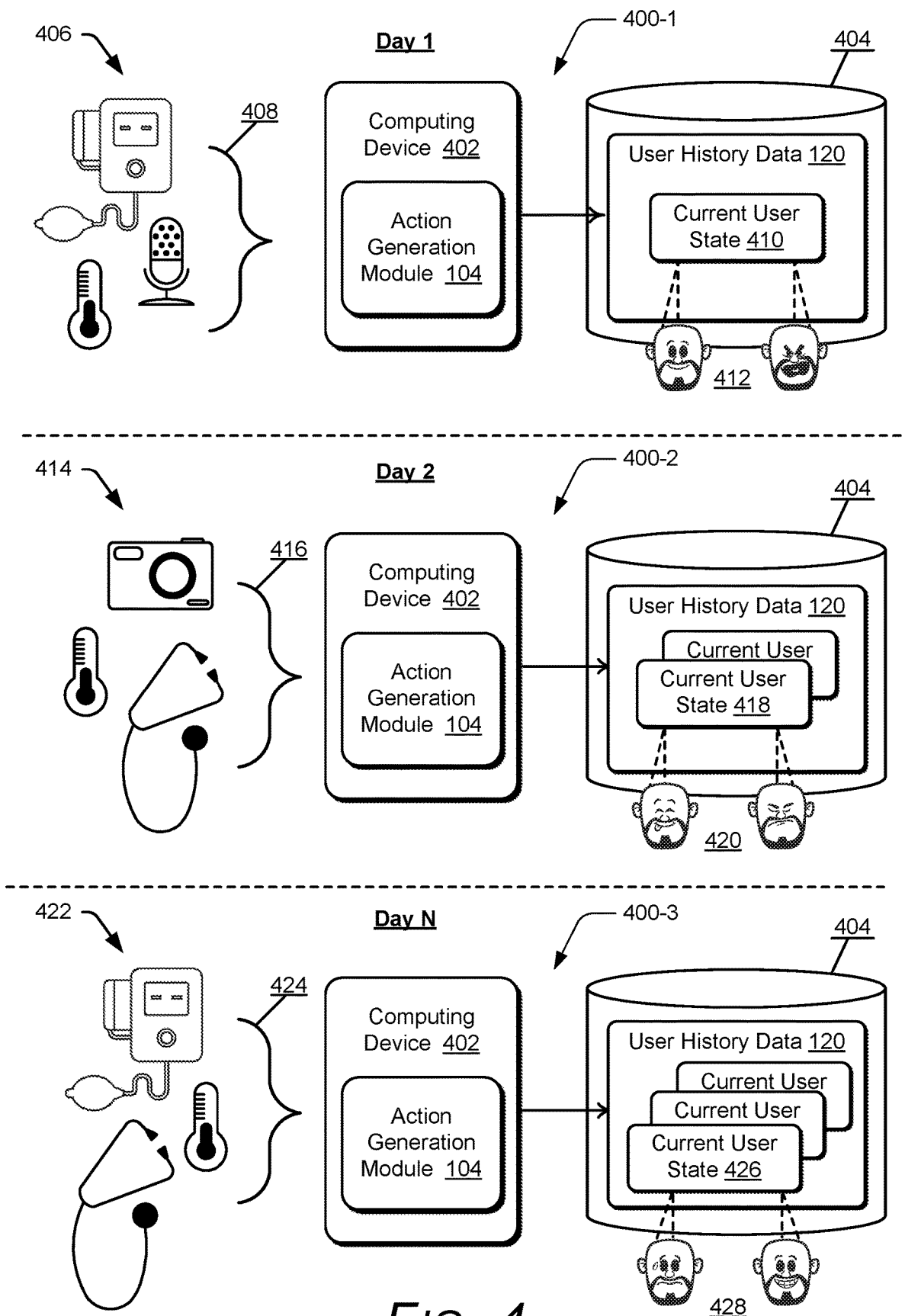
FIG. 4 illustrates an example environment in which aspects of generating action suggestions based on a change in user mood can be implemented.

FIG. 4 illustrates an example environment 100 in which a progression of events implements aspects of generating action suggestions based on a change in user mood. These events occur in an example environment 400 that includes a computing device 402. The example environment 400 is represented at three arbitrary points in time that are labeled as example environment 400-1, example environment 400-2, and example environment 400-3, respectively. The example environment 400-1 corresponds to a first point in time labeled as "Day 1", the example environment 400-2, labeled as "Day 2" corresponds a second point in time, and the example environment 400-3 corresponds to an arbitrary point in time labeled as "Day N", where "N" is an arbitrary number. Collectively, the example environment 400-1, the example environment 400-2, and the example environment 400-3 embody the example environment 400.

The computing device 402 can be any suitable type of computing device that implements the action generation module 104 as shown and described with reference to FIG. 1 to generate action suggestions based on a change in user mood. In implementations, the computing device 402 is representative of the computing device 102 (FIG. 1), the computing device 202 (FIG. 2), the server computing device 206 (FIG. 2), and/or the computing device 302 (FIG. 3). The example environment 400 also includes the user history data 120 (FIG. 1) that is maintained on a storage device 404, where example storage devices are described with reference to the example device 1100 of FIG. 11. In implementations, the computing device 402 implements, maintains, and/or updates the user history data. While the user history data 120 is illustrated as residing on a storage device external to the computing device 402 in the example environment 400, implementations of the computing device 402 can store the user history data 120 internally.

The example environment 400-1 represents a point in time (e.g., "Day 1") where the computing device 402 is positioned at a location that includes devices 406. The devices 406 can be any suitable type of device that has the ability to collect and exchange data with another device, such as any combination of IoT devices external to the computing device 402 and/or sensors internal to the computing device 402. In the example environment 400-1, the computing device 402 has established a communication link to some or all of the devices 406, such as over a wireless network, a wired network, an internal communication bus, via shared memory, etc. The devices 406 include a blood pressure sensor, a body temperature sensor, and an audio sensor (e.g., a microphone), each of which includes an ability to collect and communicate sensor data as input 408 to the computing device and/or the action generation module 104. For example, the body temperature sensor can reside internal to a smart watch that corresponds to the computing device 402. The body temperature sensor can continuously and/or periodically collect a body temperature and transmit the body temperature sensor data to the action generation module as the input 408. As another example, the microphone can reside internal to the computing device 402, and continuously and/or periodically capture audio of a surrounding environment. The microphone can then forward the audio sensor data and/or metrics associated with audio sensor data, such as an audio level metric, to the action generation module as the input 408. As yet another example, the blood pressure sensor can represent an IoT device that resides external to the computing device 402 that collects and forwards blood pressure sensor data to the action generation module as the input 408.

In response to receiving the input 408, implementations of the action generation module determine a current user state 410 that can include a user mood state 412. For example, in response to receiving the audio sensor data, implementations of the action generation module can analyze the audio sensor data using various algorithms that identify various audio characteristics, such as an intensity, a pitch, a formant, a frequency, etc. The action generation module can then analyze these audio characteristics using machine-learning algorithms to determine the user mood state 412. As another example, the action generation module can receive blood pressure measurements, and compare the current measurements to a baseline to identify if the user has an elevated blood pressure, normal blood pressure, lower blood pressure, and use this data to determine the user mood state 412. In some implementations, the action generation module analyzes sensor information from multiple devices to determine the user mood state, such as analyzing a blood pressure measurement from a first device with a heartrate measurement from a second device.

The user mood state 412 generally represents any type or combination of mood state, such as a happy mood state, an angry mood state, a frustrated mood, a silly mood, a sad mood, an excited mood, and so forth. Alternately or in addition, the action generation module 104 can classify the user mood state 412 as being a contented mood state or a discontented mood state. For example, the action generation module can classify positive mood states, such as the happy mood state, the silly mood state, and the excited mood state, as contented mood states. The action generation module can also classify negative mood states, such as the angry mood state, the frustrated mood state, and the sad mood state, as discontented mood states. The action generation module 104 can then aggregate the user history data 120 with the current user state 410, such as by storing the user mood state as a user state parameter within the user history data. This can include storing timestamps, date information, location information, and so forth, with the current user state in the user history data.

The example environment 400-2 corresponds to a second point in time (e.g., "Day 2"), where the computing device 402 resides at a location that includes devices 414. The location of the example environment 400-2 can be the same location as that described with respect to the example environment 400-1, or a different location. The devices 414 can include any combination of devices, such as IoT devices external to the computing device 402 and/or sensors internal to the computing device 402. The devices 414 can include some or all of the devices 406. In the example environment 400-2, the devices 414 include a camera, a body temperature sensor, and a heartrate sensor, each of which has an ability to collect and communicate sensor data as input 416 to the computing device 402 and/or the action generation module 104. For example, the camera can reside internal to the computing device and collect still or video images of a surrounding area. The camera can then forward the images to the action generation module 104 as part or all of the input 416. As another example, the heartrate monitor can be a peripheral device of the computing device 402 that collects heartrate measurements that are communicated as the input 416.

The action generation module analyzes the input 416 from the devices to determine a current user state 418 that can include a user mood state 420. In implementations, the action generation module can apply machine-learning algorithms to the images received from the camera as a way to identify moods, emotions, etc., such as facial recognition algorithms. The action generation module 104 can then aggregate the user history data 120 with the current user state 418, such as by storing the user mood state as a user state parameter within the user history data. This can include storing timestamps, date information, location information, and so forth, with the current user state in the user history data. In the example environment 400-2, the user history data 120 has been updated to include the current user state 410 determined in the example environment 400-1, and the current user state 418.

The example environment 400-3 corresponds to an arbitrary point in time (e.g., "Day N"), where the computing device 402 is positioned at a location that includes devices 422. The devices 422 can be any combination of external and/or internal devices associated with the computing device that have an ability to collect and communicate sensor data as input 424 to the computing device 402 and/or the action generation module 104. Similar to that described with reference to the example environment 400-1 and/or the example environment 400-2, the action generation module 104 analyzes the input 424 to determine a current user state 426 that can include a user mood state 428 as described herein. In turn, the action generation module adds the current user state 426 to the user history data 120. In the example environment 400-3, the user history data 120 has been updated to include the current user state 410, the current user state 418, and the current user state 426. Thus, the action generation module can receive sensor data from a variety of devices and/or sensors, determine a current user state based on the sensor data, and aggregate the user history data to include a collection of user state data that has been gathered over an arbitrary duration.

By gathering environment data from various IoT devices, the action generation module can determine an environment context and correlate the environment context to a user mood. This provides additional insight on environmental changes that influence a user's mood relative to determining the user's mood by only analyzing sensor data without environment context. For example, without considering an environment context that indicates a user is at a gym exercising, an elevated heartrate may be misinterpreted as a medical emergency based on current sensor data. Without considering past environment context and user moods, the misinterpretation of the medical emergency can also lead to an action suggestion that is counter-intuitive or non-productive to the user (e.g., a recommendation to limit activity). The inclusion of environment context provides additional insight that indicates why the heartrate is elevated and improves the action suggestion generated by the action generation module. With the additional environment context, the action generation module more accurately interprets the elevated heartrate as being correlated to exercise instead of a medical emergency, and can make an action suggestion based on exercise activities (e.g., recommend to continue exercising for 20 minutes, recommend to drink water when exercise activity completes, etc.).

Figure 5:
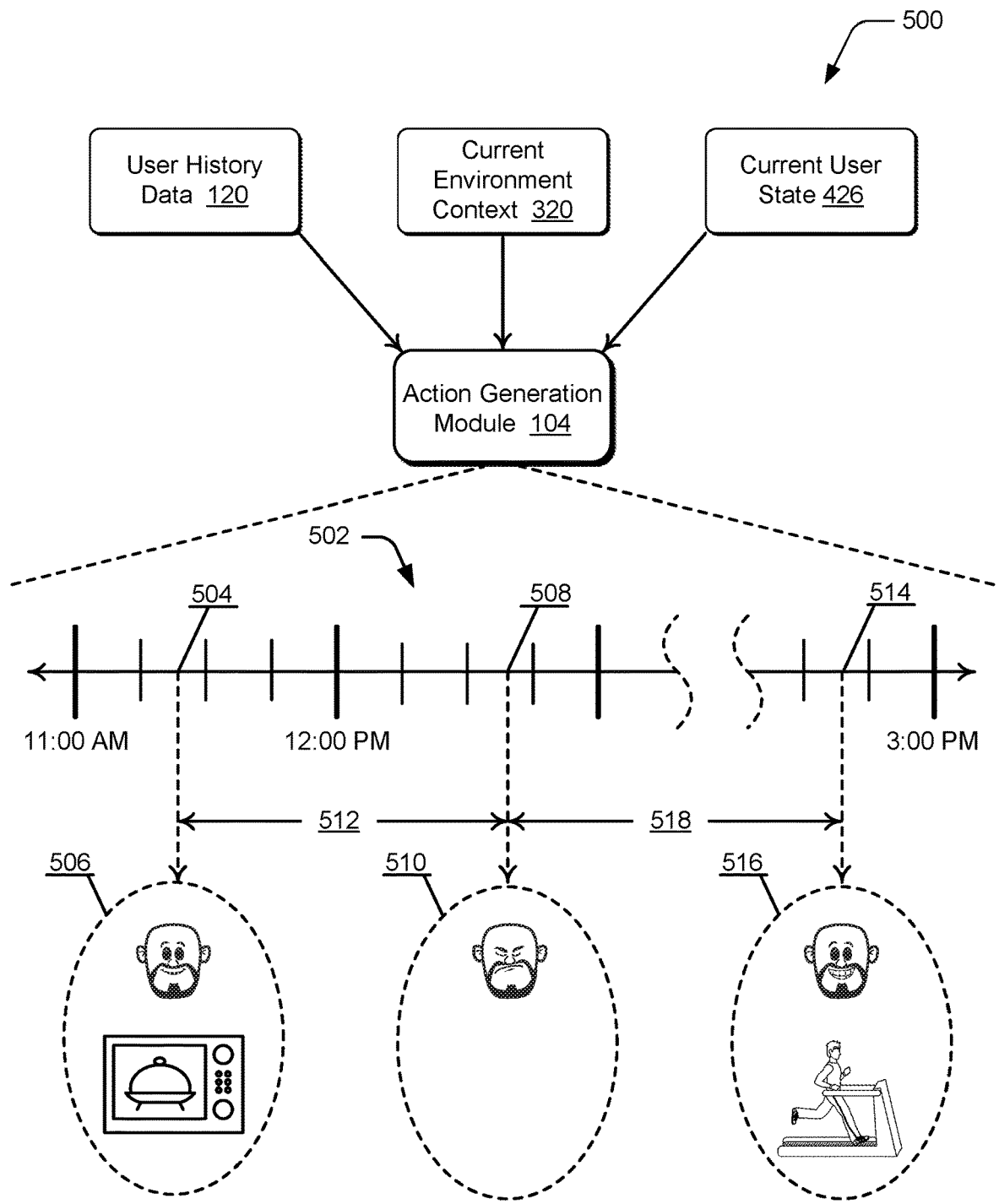
FIGS. 5-7 illustrate example features of generating action suggestions based on a change in user mood in accordance with one or more implementations.

FIG. 5 illustrates example features of generating action suggestions based on a change in user mood as described herein through an example 500. The example 500 includes the action generation module 104 and the user history data 120 as shown and described with reference to FIG. 1. The example 500 also includes the current environment context 322 (FIG. 3), and the current user state 426 (FIG. 4). In implementations, the action generation module 104 analyzes data from any combination of the user history data 120, the current environment context 322, and/or the current user state 426 to identify correlations between user mood states and environment context parameters. This can include identifying correlations between a current user state and the current environment context and/or identifying correlations between a sequence of user mood state changes and a sequence of environment context parameters.

The example 500 includes a timeline 502 that represents an arbitrary duration over which a collection of data has been gathered, such as a collection of data stored in the user history data 120. The action generation module 104 can analyze the collection of data using machine-learning algorithms to identify correlations between a user mood and environment context parameters as described herein. For example, at time 504, the action generation module can identify a correlation 506 between the user having a positive and/or contented mood state and an environment context parameter that indicates a user activity (e.g., an eating activity). In turn, the action generation module can update the user history data to include the correlation 506 and/or linkages between the user activity and the positive and/or contented mood state.

At time 508, the action generation module can identify that a change in user mood has occurred, and correlate the change in user mood to a change in user activity. For example, the action generation module can identify a correlation 510 between a lethargic user mood state and the user activity at the time 508 (e.g., an inactive state). The action generation module can also determine that the lethargic user mood state corresponds to a transition from a positive and/or contented mood state to a negative and/or discontented mood state. In implementations, the action generation module determines other correlations between the data at the time 504 and the time 508, such as a correlation that the user activity has transitioned from an eating activity to an inactive state, a correlation that the change in user mood occurs over a duration 512, etc. Thus, in determining the correlation 510, the action generation module 104 can identify links between the user moods and user activities that occur at the time 504 and at the time 508. In turn, the action generation module 104 can update the user history data to include these linkages.

At time 514, the action generation module 104 identifies a correlation 516 between an excited user mood and an exercise activity. The action generation module can also determine that the excited user mood corresponds to a change in user mood state that occurs at a duration 518 after the lethargic user mood at time 508. In implementations, the action generation module 104 identifies the changes in user moods between the time 504, the time 508, and the time 514 as a sequence of user mood state changes. The action generation module can also correlate the sequence of user mood state changes to a sequence of environment context parameters, such as by applying various machine-learning algorithms as described herein. In the example 500, the sequence of environment context parameters corresponds to a sequence of user activities (e.g., an eating activity, an inactive state, an exercise activity), but alternate or additional types of environment context parameters can be identified as well, such as an audio level, a luminance level, a location, people who are present, etc. The action generation module can also update the user history data to link the sequence of the user mood state changes with the sequence of the environment context parameters, and can base future action suggestions on this information.

Figure 6:
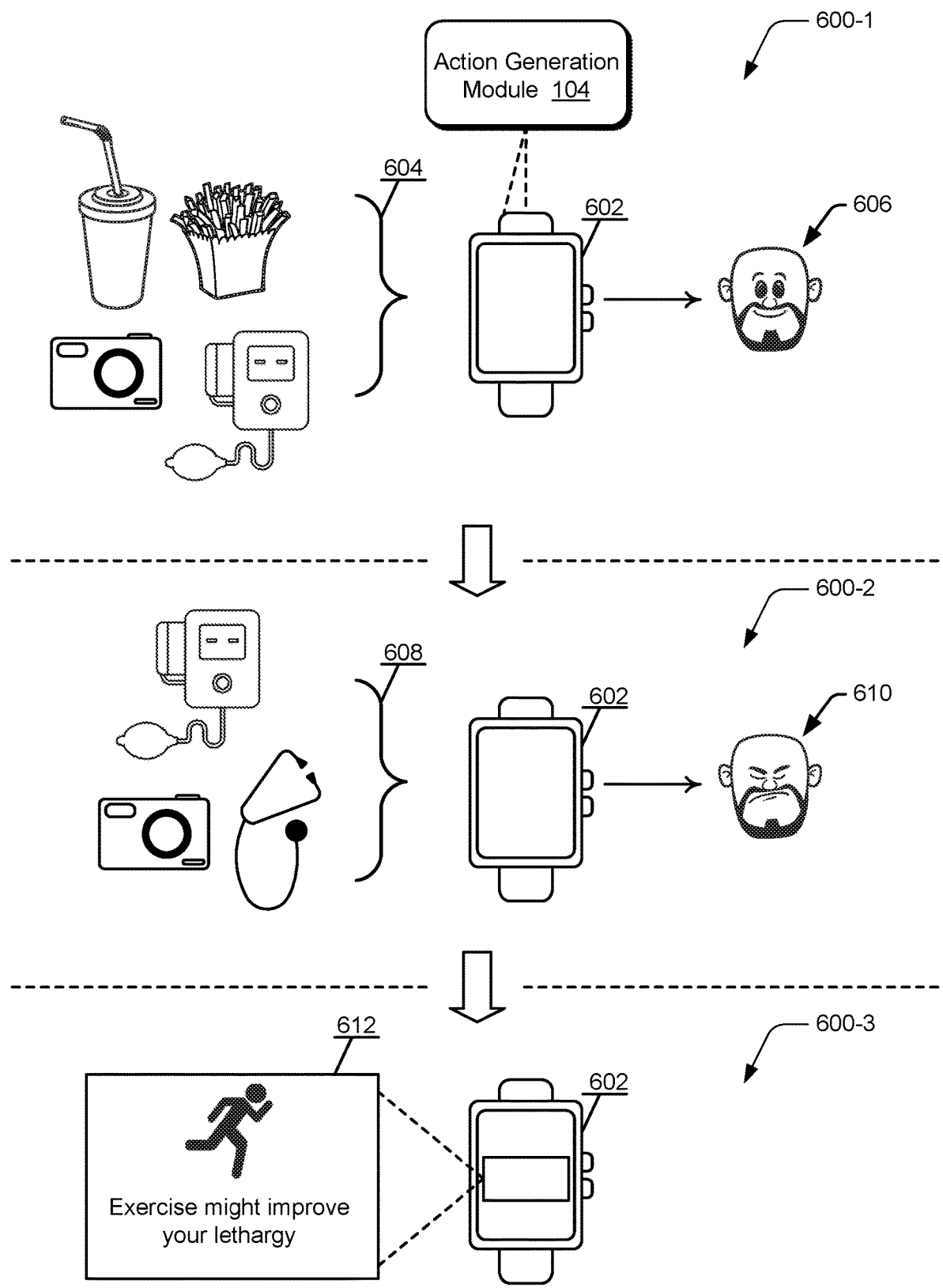

FIG. 6 illustrates example features of generation action suggestions based on a change in user mood through a progression of events in an example environment 600. The example environment 600 includes an example computing device 602 in the form of a wearable smart watch that implements features of the action generation module 104. The example environment 600 is represented at three arbitrary points in time that are labeled as example environment 600-1, example environment 600-2, and example environment 600-3, respectively. Collectively, the example environment 600-1, the example environment 600-2, and the example environment 600-3 embody the example environment 600.

In the example environment 600-1, the action generation module 104 receives input 604 from various devices and/or sensors. For example, the input 604 can include environment data from IoT devices that provide location data, food item data, nutritional data, etc. Alternately or in addition, the input 604 can include sensor data, such as an image, biometric data, etc. The action generation module 104 analyzes the input 604 and determines a current user state 606 associated with a user, where the current user state 606 corresponds to a positive and/or contented mood state. In implementations, the action generation module correlates the current user state 606 to a current environment context, and updates the user history data to include the correlation linkages.

In the example environment 600-2, the action generation module receives input 608 that can be any combination of environment data and/or sensor data. The action generation module 104 analyzes the input 608, determines a current user state 610 associated with the user, and classifies the current user state as a negative and/or discontented mood state. The action generation module also identifies that the current user state 610 corresponds to a transition from the positive and/or contented mood state to the negative and/or discontented mood state, and determines to generate an action suggestion based on the negative and/or discontented mood state. In implementations, the action generation module can analyze the user history data to identify past sequences of user moods changes that correlate to a currently identified sequence of user mood state changes, such as the sequence identified between the current user state 606 and the current user state 610. For example, the action generation module can correlate the currently identified sequence of user mood state changes to the sequence of user mood state changes identified and described with reference to FIG. 5. In response to identifying this correlation, the action generation module can then analyze the environment context parameters associated with the past sequence of user mood state changes to determine environment context parameters that pertain to the currently identified sequence of user mood state changes.

In the example environment 600, the action generation module 104 correlates a current sequence of environment context parameters to the current user state 606 and the current user state 610: an eating activity followed by an inactive state. In analyzing the user history data, the action generation module also determines that the current sequence of environment context parameters correlate to the past sequence of environment context parameters as shown and described with reference to FIG. 5. The past sequence of user mood changes and the past sequence of environment context parameters also indicate that following a negative and/or discontented mood state (e.g. a lethargic mood) with an exercise activity successfully modified the user mood state to a positive and/or contented mood state as determined by the correlation 516. In the environment 600-3, the action generation module 104 generates action suggestion 612 based on the correlation 516, and the related mood changes and environment context parameters as described herein. Thus, the action generation module can analyze past sequences of user mood changes and the correlated past sequence of environment context parameters to generate an action suggestion. In the example environment 600-3, the computing device 602 automatically displays the action suggestion 612 on a display device, but alternate implementations display the action suggestion in response to user input.

Figure 7:
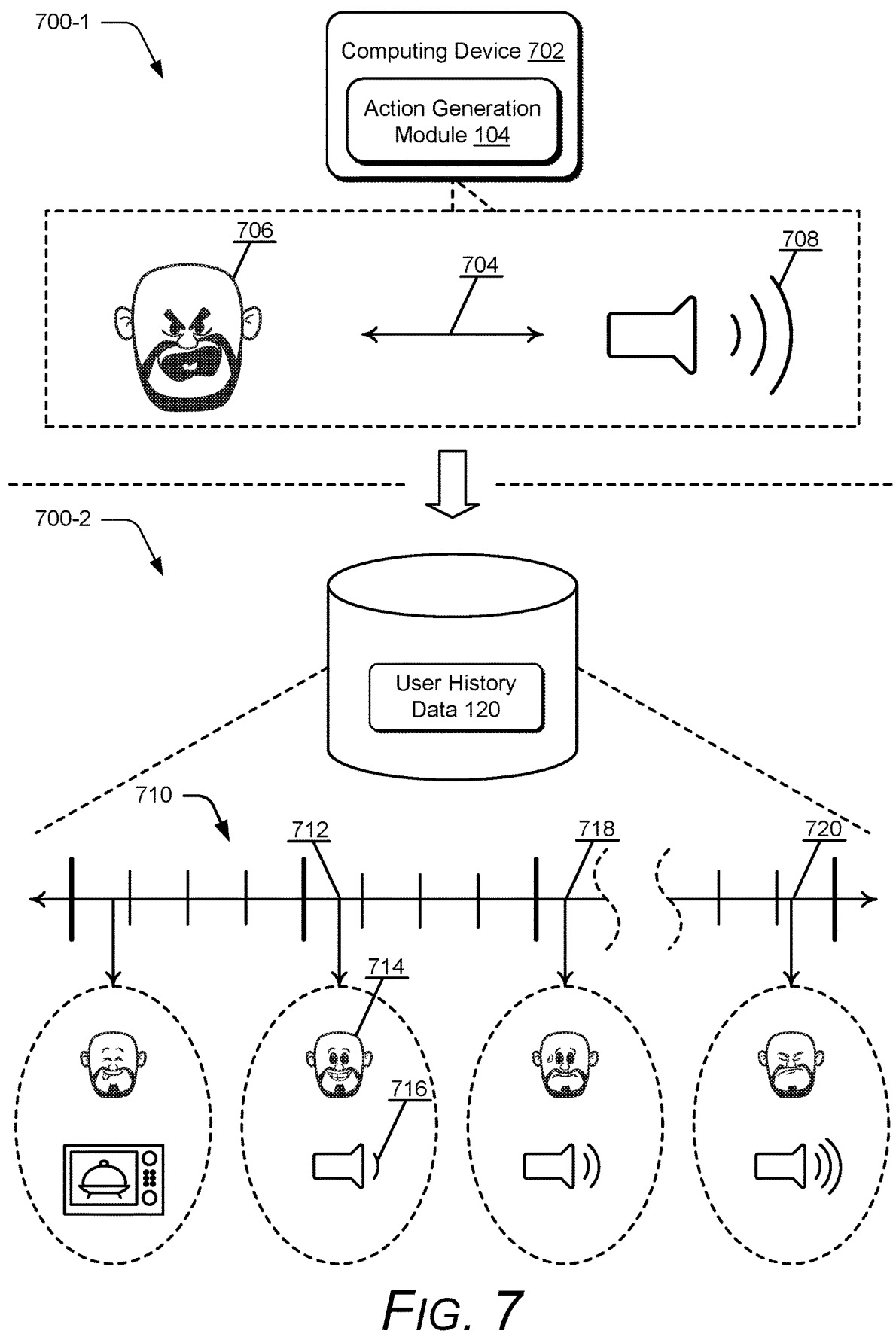

FIG. 7 illustrates example features of generation action suggestions based on a change in user mood through a progression of events in an example environment 700. The example environment includes an example computing device 702 that implements features of the action generation module 104 and/or the user history data 120 as shown and described with reference to FIG. 1. The example environment 700 is represented at two arbitrary points in time that are labeled as example environment 700-1 and example environment 700-2, respectively. Collectively, the example environment 700-1 and the example environment 700-2 embody the example environment 700.

In the example environment 700-1, the action generation module 104 has identified a correlation 704 between a current user state 706 and a current environment context 708. As described herein, the action generation module 104 can apply various machine-learning algorithms to input sensor data and/or input environment data to determine the current user state 706, that the current user state corresponds to a negative and/or discontented mood state, and that the negative and/or discontented mood state correlates to an audio level environment context parameter.

Implementations of the action generation module 104 analyze the user history data 120 to identify point(s) in time that have environment context parameters that can be used to generate an action suggestion. This can include analyzing the user history data to identify past user mood states, and identify environment differences based on the past user mood states. In the example environment 700-2, the aggregated data included in the user history data 120 is generally denoted as timeline 710. The action generation module can analyze the user history data to find a point in time that corresponds to a positive and/or contented user mood, such as by analyzing the user state parameters at varying points in time. At time 712, the action generation module determines that user state parameter 714 corresponds to a positive and/or contented mood state. In response to finding the positive and/or contented mood state, the action generation module analyzes environment context parameters at the time 712 to identify an environmental difference that has a high probability of causing a change in user mood.

At the time 712, the action generation module 104 determines that the audio level in the current environment context 708 has a higher dB metric relative to the audio level included in environment context parameter 716, and determines the audio level to be an environment difference. In implementations, the action generation module 104 uses the environment context parameter 716 as a basis for an action suggestion as described herein. The action generation module 104 can alternately or in addition track the audio level at time 718 and at time 720, as well as the user mood states, and identify a correlation that indicates the user mood state progresses through negative and/or discontented mood states as the audio level increases. Thus, the action generation module can analyze the user history data to find a point in time that corresponds to a different user mood state than a current user state, use that point in time to identify an environment difference that correlates to the change in the user mood, and then analyze the environment difference to determine environment context parameters to use in generation an action suggestion.

In implementations, the action generation module 104 can identify IoT device changes that can be made to one or more of the IoT devices as part of the action suggestion. In the environment 700-2, the action generation module 104 identifies the environmental difference that corresponds to changes in the audio level at the time 712 and a current audio level corresponding to the current environment context 708. As described herein, the action generation module can generate an action suggestion that indicates to modify the current audio level based on this environment difference. Alternately or in addition, the action generation module can communicate with a corresponding IoT speaker device to modify the audio level. For instance, the action generation module 104 can communicate a command over the network 114 to an IOT speaker device of the IoT devices 112 to lower the current audio level. The action generation module can include an indication of the audio level in the command and/or the IoT speaker device can automatically determine the modified audio level. Thus, aspects of generating action suggestions based on a change in user mood can determine modifications to IoT device states and/or initiate the modifications to the IoT device states, such as by the action generation module issuing commands to the IoT devices.

By analyzing a history of data (e.g., data that has been collected and updated over a duration), the action generation module can generate action suggestions that are based on stable and/or repeated contextual information about a user, rather than inconsistent data and/or anomalies. In implementations, the action generation module can apply a time series correlation analysis over varying long-term durations (e.g., hours, days, weeks, etc.) to determine stable trends associated with the user, such as a trend where the user repeatedly eats food with low nutritional value, feels content for the first 30 minutes, but then transitions to discontent. In implementations that analyze short-term durations (e.g. instantaneous, seconds, less than 30 minutes), the generated action suggestion may indicate to continue eating food nutritional value since the user feels content in the short-term after this activity. Conversely, a long-term analysis can identify effects with a high level of correlation to the activity that take more time to manifest. In turn, the action generation module can base an action suggestion on the long-term effects, thus providing the user with an action suggestion that is more likely to address a mood change.

The inclusion of environment data from external devices (e.g., IoT devices) improves the quality of an action suggestion generated by an action generation module, where the quality of the action suggestion corresponds to an effectiveness of the action suggestion in modifying a user's mood and/or a duration of the modified mood. For example, the analysis of sensor data can determine when a user has had a low quality of sleep and/or that the user low quality of sleep corresponds to irritability. By including environment data in the analysis, as well as a long-term analysis, implementations can correlate the low quality of sleep to an activity, such as watching television or eating acidic food prior to sleeping. In implementations, the action generation module can weight and/or prioritize data analyzed to generate an action suggestion based on user history data as described herein.

FIG. 8 illustrates an example weighting table 800 and an example weighting table 802 that can be used to implement features of generating action suggestions based on a change in user mood as described herein. In implementations, an action generation module can dynamically generate portions or all of the weighting based on user history data. Alternately or in addition, the weighting data can be static and/or fixed tables that are installed and/or provided to the action generation module.

The weighting table 800 represents static weighting data in the form of a table that assigns various weights to different types of data. For example, the weighting table 800 assigns biometric data with a weight of 0.75 and peer data a weight of 0.25. In implementations, an action generation module can apply these weightings when analyzing sensor data, environment data, and/or user history data to give a user's biometric data more influence on the resulting analysis output relative to peer data.

The weighting table 802 represents dynamic weighting data in the form of a dynamic table based on location information. For example, the action generation module can track locations associated with receiving environment data from IoT devices and/or sensor data, and generate the weighting table 802 to prioritize data associated with locations that are more frequently visited over locations that are less frequently visited. Thus, in the weighting table 802, location C is given the highest weighting and/or priority value relative to other locations based on having the highest number of visits relative to other locations. Location A is given the lowest weighting based on having the lowest number of visits. As new visits to locations are tracked, the priority and/or weighting values can change. For example, at some point in time, the action generation module can determine that Location E has a total number of visits that exceeds Location C, and reprioritize the weights assigned to each location. Other types of dynamic weighting data can be applied to the user history data, environment data, sensor data, environment context data, etc., as well, such as Gaussian weighting functions, root-mean-square (RMS) weighting functions, Monte Carlo methods, weighted averages, bilinear forms, orthogonal polynomials, etc.

Figure 9:
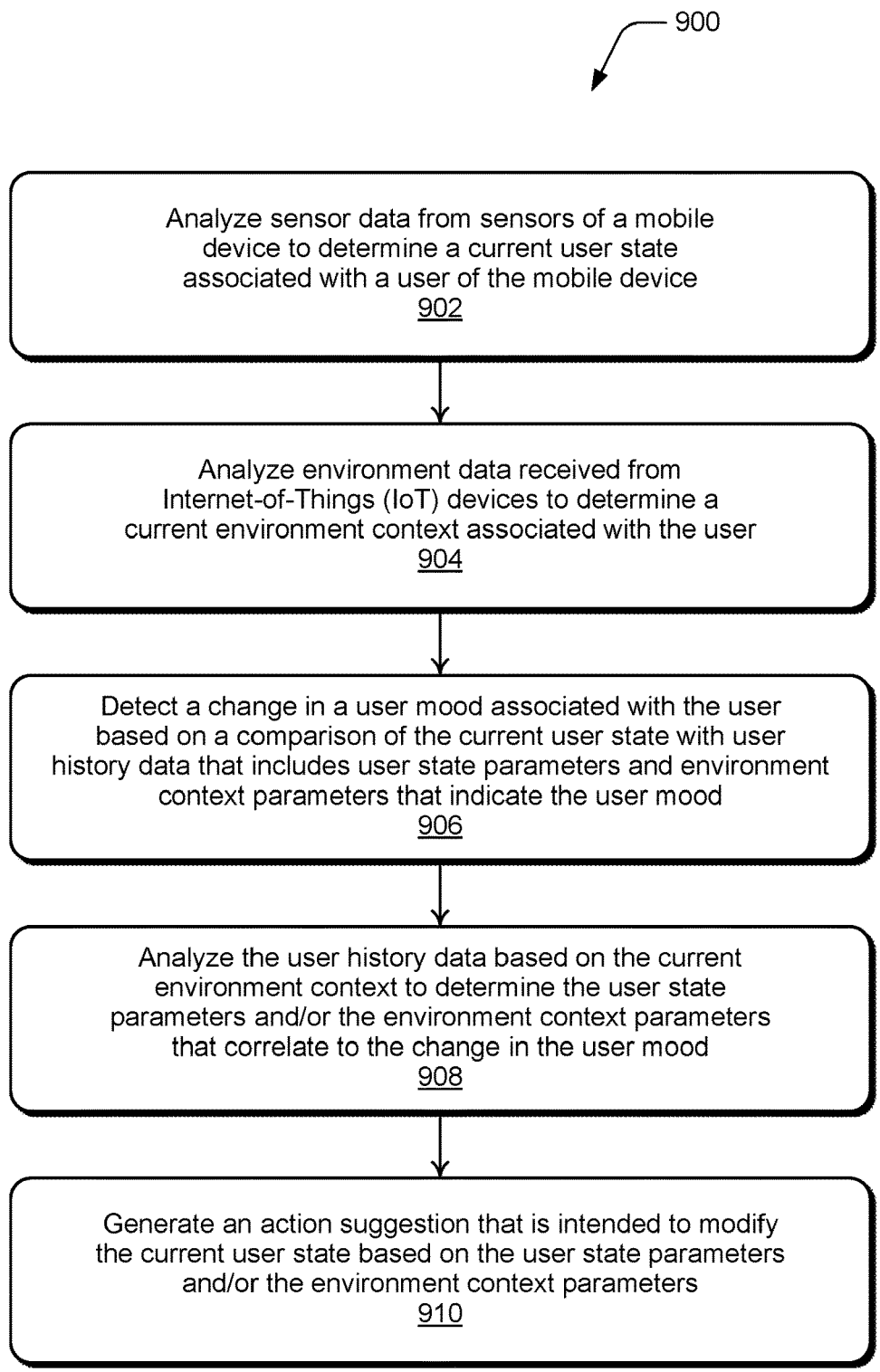
FIG. 9 illustrates an example method for generating action suggestions based on a change in user mood in accordance with one or more implementations of the techniques described herein.

FIG. 9 illustrates an example method 900 for generating action suggestions based on a change in user mood, and is generally described with reference to an action generation module as shown and described with reference to FIGS. 1-8. The order in which the method is described is not intended to be construed as a limitation, and any number or combination of the method operations can be combined in any order to implement a method, or an alternate method.

At 902, sensor data from sensors of a mobile device is analyzed to determine a current user state associated with a user of the mobile device. For example, the action generation module 104 implemented by the computing device 102 analyzes the sensor data 108 produced by the sensors 106 to determine a current user state of a user. In implementations, the action generation module 104 of the computing device 102 (e.g., a mobile device) analyzes images captured by a camera sensor to identify facial expressions, and the current user state of the user of the device is determined based on the facial expressions. Alternately or in addition, the action generation module 104 analyzes audio data from microphones to determine one or more audio characteristics, such as an intensity, a pitch, a formant, or a frequency, and the current user state of the user of the device is determined based on the audio characteristics.

At 904, environment data received from IoT devices is analyzed to determine a current environment context associated with the user. For example, the action generation module 104 analyzes the environment data 110 produced by the IoT devices 112 to determine a current environment context associated with the user, such as a user location, a current user activity, and so forth. In an example, the action generation module 104 receives barcode information that is associated with a food item, and determines a health metric associated with the food item by using the barcode information to collect nutritional information. In implementations, the action generation module 104 determines the health metric as part of determining the current context environment. Alternately or additionally, the action generation module 104 extracts location information from the environment data 110, and prioritizes the environment data based on the location information.

At 906, a change in a user mood associated with the user is detected based on a comparison of the current user state with user history data that includes user state parameters and environment context parameters that indicate the user mood. For example, the action generation module 104 detects a change in user mood associated with the user based on a comparison of the current user state 116 with the user history data 120. In implementations, the user history data 120 includes the user state parameters 122 and the environment context parameters 124 that indicate the user mood over a duration, such as hours, a day, a week, a number of years, etc. In implementations, the action generation module 104 detects the change in mood of the user based on a transition from a positive and/or contented mood state to a negative and/or discontented mood state of the user.

At 908, the user history data is analyzed based on the current environment context to determine the user state parameters and/or the environment context parameters that correlate to the change in the user mood. For example, the action generation module 104 analyzes the user state parameters 122 in the user history data 120 to identify a point in time, where a user state at the point in time differs from the current user state 116. Alternately or in addition, action generation module 104 analyzes the environment context parameters 124 in the user history data 120 at the point in time to identify an environmental difference. In implementations, the action generation module 104 applies weighting data to the user history data 120 effective to prioritize the user history data. For example, the action generation module 104 prioritizes the environment context parameters 124 in the user history data 120 by prioritizing the environment context parameters 124 associated with more frequently visited locations higher than environment context parameters 124 associated with less frequently visited locations, as described herein.

At 910, an action suggestion is generated that is intended to modify the current user state based on the user state parameters and/or the environment context parameters. For example, the action generation module 104 generates the action suggestion 128 based on the user state parameters 122 and/or the environment context parameters 124 that correlate to the change in user mood, and the action suggestion 128 is intended to modify the current user state 116 of the user.

Figure 10:
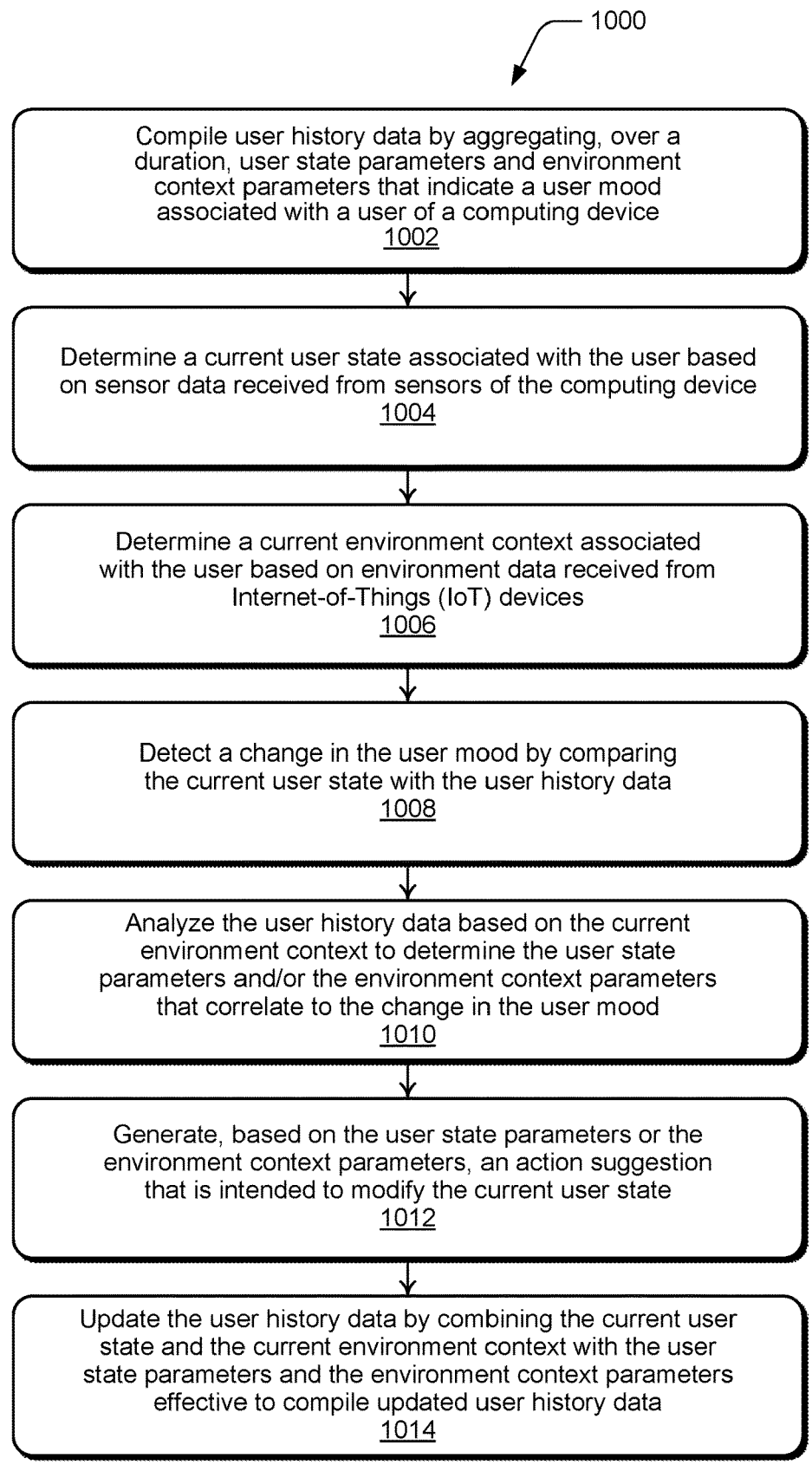
FIG. 10 illustrates an example method for generating action suggestions based on a change in user mood in accordance with one or more implementations of the techniques described herein.

FIG. 10 illustrates an example method 1000 for generating action suggestions based on a change in user mood, and is generally described with reference to an action generation module as shown and described with reference to FIGS. 1-9. The order in which the method is described is not intended to be construed as a limitation, and any number or combination of the method operations can be combined in any order to implement a method, or an alternate method.

At 1002, user history data is compiled by aggregating, over a duration, user state parameters and environment context parameters that indicate a user mood associated with a user of a computing device. For example, the action generation module 104 implemented by the computing device 102 compiles the user history data 120 by aggregating the user history data 120 with the user state parameters 122 included in a current user state 116 and environment context parameters 124 included in the current environment context 118. In implementations, the action generation module 104 identifies a sequence of user mood state changes based on the user state parameters 122, and correlates the user history data 120 with the sequence of the user mood state changes to identify a sequence of the environment context parameters 124 that are associated with the sequence of the user mood state changes. The action generation module 104 then aggregates the user history data 120 to link the sequence of the user mood state changes with the sequence of the environment context parameters.

At 1004, a current user state associated with the user is determined based on sensor data received from sensors of the computing device. For example, the action generation module 104 determines the current user state 116 based on an analysis of the sensor data 108 received from the device sensors 106. At 1006, a current environment context associated with the user is determined based on environment data received from IoT devices. For example, the action generation module 104 determines the current environment context 118 associated with the user from an analysis of the environment data 110 received from the IoT devices 112.

At 1008, a change in user mood is detected by comparing the current user state with the user history data. For example, the action generation module 104 detects the change in user mood by comparing the current user state 116 with the user state parameters 122 included in the user history data 120. Alternately or in addition, the action generation module 104 detects a transition from a positive/contented mood state to a negative/discontented mood state of the user, and/or a transition from a negative/discontented mood state to a positive/contented mood state of the user.

At 1010, the user history data is analyzed based on the current environment context to determine user state parameters and/or the environment context parameters that correlate to the change in user mood. For example, the action generation module 104 analyzes the user history data 120 to determine the user state parameters 122 and/or the environment context parameters 124 that correlate to the change in user mood 126. In implementations, the action generation module 104 analyzes the environment context parameters 124 based on the current environment context 118 to determine an environment difference. For example, the action generation module 104 analyzes the user state parameters 122 to find a point in time that corresponds to a positive and/or contented user mood state of the user. The action generation module 104 then analyzes the environment context parameters 124 at the point in time and based on the current environment context 118 to determine an environment difference that correlates to the change in the user mood 126.

At 1012, an action suggestion is generated based on the user state parameters or the environment context parameters, where the action suggestion is intended to modify the current user state. For example, the action generation module 104 generates the action suggestion 128 based on the user state parameters 122 or the environment context parameters 124, and the action suggestion 128 is intended to modify the current user state of the user, such as to indicate to the user that exercise may improve a lethargic mood. In implementations, the action generation module 104 generates the action suggestion 128 based on the user state parameters 122 and/or the environment context parameters 124 as described herein.

At 1014, the user history data is updated by combining the current user state and the current environment context with the user state parameters and the environment context parameters effective to compile updated user history data. For example, the action generation module 104 updates the user history data 120 with the current user state 116 and/or the current environment context 118 to compile updated user history data. In implementations, the action generation module 104 identifies a correlation between the current user state 116 and a current activity identified by the current environment context 118, and updates the user history data 120 by adding the correlation to the user history data. The action generation module 104, for example, determines a current user state 116 based on heartbeat information included in the environment data 110. In implementations, the action generation module 104 also extracts an activity identifier from the environment data 110, where the current activity identifier is assigned as a current environment parameter of the current environment context 118. The action generation module 104 then identifies a link between the exercise activity identifier and the current user state 116, and updates the user history data 120 to include the link between the exercise activity identifier and the current user state 116.

Figure 11:
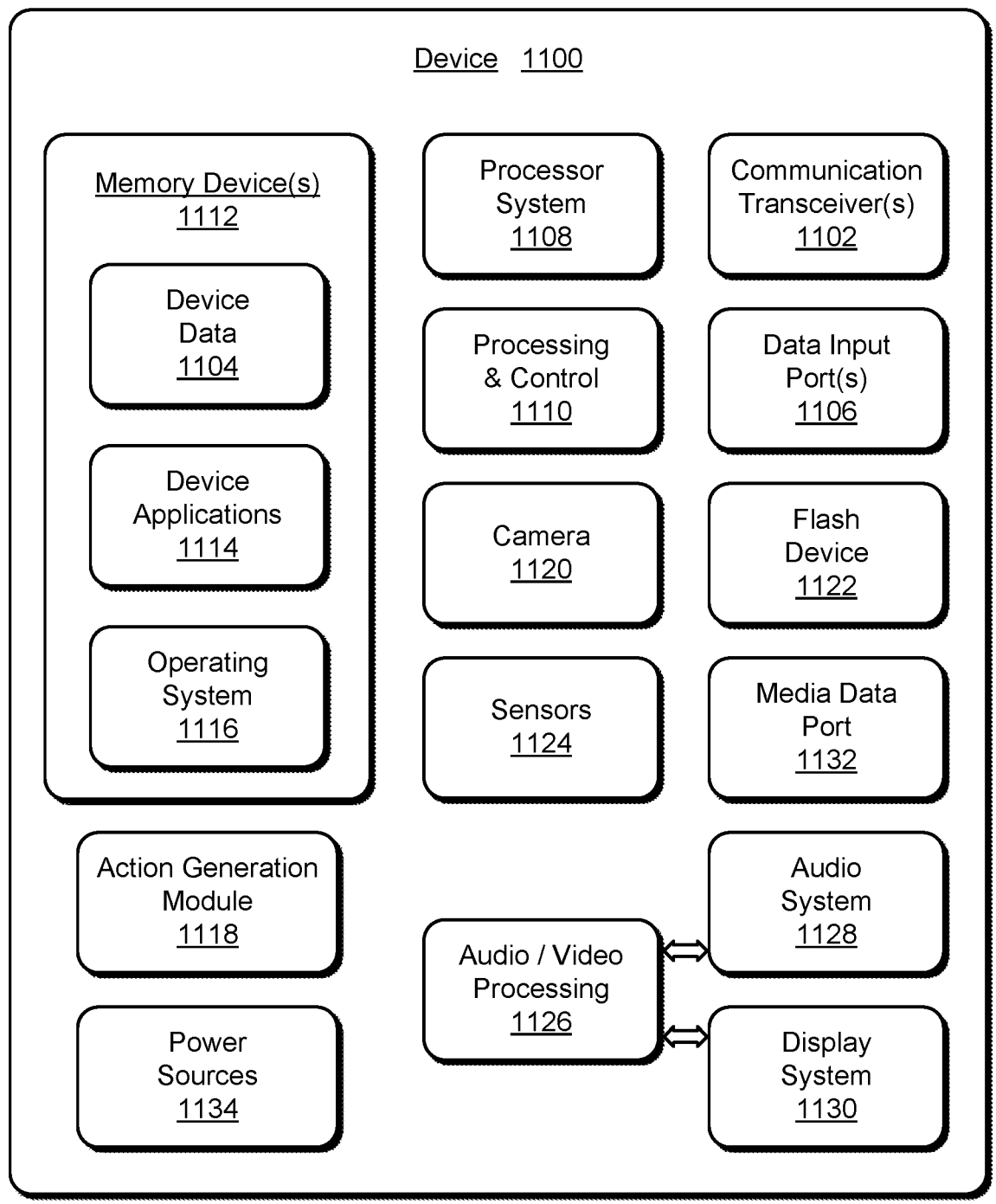
FIG. 11 illustrates various components of an example device that can implement aspects of generating action suggestions based on a change in user mood.

FIG. 11 illustrates various components of an example device 1100, which can implement examples of generating action suggestions based on a change in user mood. The example device 1100 can be implemented as any type of client device, mobile phone, tablet, communication device, wearable device, entertainment device, gaming device, media playback device, and/or other type of device. For example, the computing device 102, the computing device 202, the server computing device 206, and/or various server devices of the network system 204 may be implemented as the example device 1100.

The device 1100 includes communication transceivers 1102 that enable wired and/or wireless communication of device data 1104 with other devices. The device data 1104 can include any of the current user state, the current environment context, the user history data, sensor data, and/or environment data that are received and/or determined. The device data can also include any of the weighting tables and/or action suggestions. Additionally, the device data can include any type of audio, video, and/or image data. Example transceivers include wireless personal area network (WPAN) radios compliant with various IEEE 802.15

(Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.16 (WiMAX™) standards, and wired local area network (LAN) Ethernet transceivers for network data communication.

The device 1100 may also include one or more data input ports 1106 via which any type of data, media content, and/or inputs can be received, such as user-selectable inputs to the device, messages, music, television content, and any other type of audio, video, and/or image data received from any content and/or data source. The data input ports may include USB ports, coaxial cable ports, and other serial or parallel connectors (including internal connectors) for flash memory, DVDs, CDs, and the like. These data input ports may be used to couple the device to any type of components, peripherals, or accessories such as microphones and/or cameras.

The device 1100 includes a processing system 1108 of one or more processors (e.g., any of microprocessors, controllers, and the like) and/or a processor and memory system implemented as a system-on-chip (SoC) that processes computer-executable instructions. The processor system may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternately or in addition, the device can be implemented with any one or combination of software, hardware, firmware, or fixed logic circuitry that is implemented in connection with processing and control circuits, which are generally identified at 1110. The device 1100 may further include any type of a system bus or other data and command transfer system that couples the various components within the device. A system bus can include any one or combination of different bus structures and architectures, as well as control and data lines.

The device 1100 also includes computer-readable storage memory 1112 that enables data storage, such as data storage devices that can be accessed by a computing device, and that provide persistent storage of data and executable instructions (e.g., software applications, programs, algorithms, functions, and the like). Examples of the computer-readable storage memory 1112 include volatile memory and non-volatile memory, fixed and removable media devices, and any suitable memory device or electronic data storage that maintains data for computing device access. The computer-readable storage memory can include various implementations of random-access memory (RAM), read-only memory (ROM), flash memory, and other types of storage memory devices in various memory device configurations. The device 1100 may also include a mass storage media device.

The computer-readable storage memory 1112 provides data storage mechanisms to store the device data 1104, other types of information and/or data, and various device applications 1114 (e.g., software applications). For example, an operating system 1116 can be maintained as software instructions with a memory device and executed by the processor system 1108. The device applications may also include a device manager, such as any form of a control application, software application, signal-processing and control module, code that is native to a particular device, a hardware abstraction layer for a particular device, and so on.

The device 1100 also includes an action generation module 1118 that implements features and aspects of generating action suggestions based on a change in user mood, and may be implemented with hardware components and/or in software, such as when the device 1100 is implemented as various computing devices as described with reference to FIGS. 1-7. In implementations, action generation module 1118 may include independent processing, memory, and logic components as a computing and/or electronic device integrated with the example device 1100.

In this example, the device 1100 also includes a camera 1120, a flash device 1122, and sensors 1124 (e.g. audio sensor, biometric sensor, etc.). Although the flash device 1122 is shown as an integrated component of the device 1100, the flash device 1122 may be implemented as an external, peripheral component of the example device.

The device 1100 also includes an audio and/or video processing system 1126 that produces audio data for an audio system 1128 and/or produces display data for a display system 1130. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 1132. In implementations, the audio system and/or the display system are integrated components of the example device. Alternatively, the audio system and/or the display system are external, peripheral components to the example device.

The device 1100 can also include one or more power sources 1134, such as when the device is implemented as a mobile device or portable camera device. The power sources may include a charging and/or power system, and can be implemented as a flexible strip battery, a rechargeable battery, a charged super-capacitor, and/or any other type of active or passive power source.

Although implementations of generating an action suggestion based on a change in user mood have been described in language specific to features and/or methods, the appended claims are not necessarily limited to the specific features or methods described. Rather, the specific features and methods are disclosed as example implementations of generating action suggestions based on a change in user mood, and other equivalent features and methods are intended to be within the scope of the appended claims. Further, various different examples are described and it is to be appreciated that each described example can be implemented independently or in connection with one or more other described examples.

The invention claimed is:

1. A method, comprising:
analyzing sensor data from sensors of a mobile device to determine a current user state associated with a user of the mobile device;
analyzing environment data received from Internet-of-Things (IoT) devices to determine a current environment context associated with the user;
detecting a change in a user mood associated with the user based on a comparison of the current user state with user history data that includes user state parameters and environment context parameters that indicate the user mood;

prioritizing the environment context parameters by applying weighting data to the environment context parameters, the weighting data prioritizes first environment context parameters associated with more frequently visited locations higher than second environment context parameters associated with less frequently visited locations;

analyzing the user history data based on the current environment context to determine at least one of the user state parameters or the environment context parameters that correlates to the change in the user mood; and generating, based on the at least one of the user state parameters or the environment context parameters, an action suggestion that is intended to modify the current user state.

2. The method of claim 1, wherein the detecting the change in the user mood comprises detecting a transition from a positive mood state to a negative mood state.

3. The method of claim 1, wherein the analyzing the user history data comprises analyzing the user history data to identify a past point in time where a past user state differs from the current user state.

4. The method of claim 1, further comprising:
identifying a correlation between the current user state and the current environment context; and
updating the user history data by adding the correlation between the current user state and the current environment context to the user history data.

5. The method of claim 1, wherein the analyzing the user history data comprises applying the weighting data to the user history data effective to prioritize the user history data.

6. The method of claim 1, wherein the analyzing the environment data received from the IoT devices comprises:
extracting location information from the environment data; and
prioritizing the environment data based on the location information.

7. The method of claim 1, wherein the analyzing the sensor data to determine the current user state comprises analyzing images captured by a camera sensor to identify facial expressions, and wherein the current user state is determined based on the facial expressions.

8. The method of claim 1, wherein the environment data received from the IoT devices includes barcode information associated with a food item, and the analyzing the environment data received from the IoT devices comprises:
determining a health metric associated with the food item by using the barcode information to collect nutritional information associated with the food item; and
generating the current environment context based on the health metric.

9. The method of claim 1, further comprising:
identifying a sequence of user mood state changes based on the user history data, the current user state, and the current environment context;
correlating the user history data, the current user state, and the current environment context with the sequence of the user mood state changes to identify a sequence of the environment context parameters that are associated with the sequence of the user mood state changes; and
updating the user history data to link the sequence of the user mood state changes with the sequence of the environment context parameters.

10. A computing device, comprising:
sensors to produce sensor data associated with a user;
a memory to maintain user history data that includes user state parameters and environment context parameters that indicate a user mood associated with the user; and
a processor system that implements an action generation module to:
determine a current user state associated with the user and a current environment context associated with the user based on the sensor data and environment data received from Internet-of-Things (IoT) devices;
detect a change in the user mood based on a comparison of the current user state with the user history data;
prioritize the environment context parameters by applying weighting data to the environment context parameters, the weighting data prioritizes first environment context parameters associated with more frequently visited locations higher than second environment context parameters associated with less frequently visited locations;
analyze the user history data based on the current environment context to determine at least one of the user state parameters or the environment context parameters that correlates to the change in the user mood; and
generate, based on the user state parameters or the environment context parameters, an action suggestion that is intended to modify the current user state.

11. The computing device of claim 10, wherein:
the environment data received from the IoT devices comprises exercise data that includes heartbeat information associated with the user; and
the action generation module is implemented to determine the current user state based on the heartbeat information.

12. The computing device of claim 11, wherein:
the exercise data includes an exercise activity identifier; and
the action generation module is implemented to:
assign the exercise activity identifier as a current environment parameter that is included in the current environment context;
identify a link between the exercise activity identifier and the current user state; and
update the user history data to include the link between the exercise activity identifier and the current user state.

13. The computing device of claim 10, wherein the action generation module is implemented to:
analyze the user history data to find a point in time that corresponds to a positive user mood state;
identify an environment difference that correlates to the change in the user mood based on the environment context parameters included in the user history data at the point in time that corresponds to the positive user mood state, and based on current environment context parameters included in the current environment context; and
determine the at least one of the user state parameters or the environment context parameters based on the environment difference.

14. The computing device of claim 10, wherein the action generation module is implemented to update the user history data with the current user state and the current environment context.

15. A method, comprising:
compiling user history data by aggregating, over a duration, user state parameters and environment context parameters that indicate a user mood associated with a user of a computing device;

determining a current user state associated with the user based on sensor data received from sensors of the computing device;

determining a current environment context associated with the user based on environment data received from Internet-of-Things (IoT) devices;

detecting a change in the user mood by comparing the current user state with the user history data;

prioritizing the environment context parameters by applying weighting data to the environment context parameters, the weighting data prioritizes first environment context parameters associated with more frequently visited locations higher than second environment context parameters associated with less frequently visited locations;

analyzing the user history data based on the current environment context to determine at least one of the user state parameters or the environment context parameters that correlates to the change in the user mood;

generating, based on the at least one of the user state parameters or the environment context parameters, an action suggestion that is intended to modify the current user state; and updating the user history data by combining the current user state and the current environment context with the user state parameters and the environment context parameters effective to compile updated user history data.

16. The method of claim 15, further comprising:
extracting location information from the environment data; and
prioritizing the environment data based on the location information.

17. The method of claim 15, wherein the determining the current user state associated with the user is based on one or more audio characteristics including at least one of: an intensity, a pitch, a formant, or a frequency.

18. The method of claim 15, wherein the updating the user history data comprises:
identifying a correlation between the current user state and a current activity identified by the current environment context; and
adding the correlation between the current user state and the current activity to the user history data.

19. The method of claim 15, wherein the analyzing the user history data comprises analyzing the user history data to identify a past point in time where a past user state differs from the current user state.

20. The method of claim 15, wherein the analyzing the user history data comprises applying the weighting data to the user history data effective to prioritize the user history data.

* * * * *